United States Patent [19]

Leibowitz et al.

[11] Patent Number: 5,776,680
[45] Date of Patent: Jul. 7, 1998

[54] DIAGNOSTIC PROBES FOR PNEUMOCYSTIS CARINI

[75] Inventors: Michael J. Leibowitz, Manalapan; Yong Liu, Piscataway, both of N.J.

[73] Assignee: University of Medicine & Dentistry of New Jersey, Newark, N.J.

[21] Appl. No.: 505,509

[22] Filed: Jul. 21, 1995

Related U.S. Application Data

[63] Continuation of Ser. No. 298,087, Aug. 31, 1994, abandoned, which is a continuation of Ser. No. 922,987, Jul. 30, 1992, abandoned.

[51] Int. Cl.$^6$ .............. C12Q 1/68; C12P 19/34; C07H 21/04
[52] U.S. Cl. .......... 435/6; 435/91.2; 536/23.74; 536/24.32; 536/24.33; 935/8; 935/78
[58] Field of Search .......... 435/6, 91.2; 536/23.74, 536/24.32, 24.33; 935/8, 77, 78

[56] References Cited

FOREIGN PATENT DOCUMENTS 8803957  6/1988  WIPO.
9102092  2/1991  WIPO.
9119005  12/1991  WIPO.

OTHER PUBLICATIONS

Erlich et al, Science (1991) 252:1643–1651.
Regensburger, J. Gen Microb (1988) 134:1197–1204.
Williams BioTechniques (1989) 17:762–768.
White et al PCR Protocols: A Guide to Methods & Applications, 1990, Innis et al, Eds, pp. 315–322.

*Primary Examiner*—Carla J. Myers
*Attorney, Agent, or Firm*—Richard R. Muccino

[57] ABSTRACT

The present invention pertains to a method for diagnosing for *Pneumocystis carinii* by detecting the presence of a nucleic acid sequence containing the 26S rRNA gene specific for *Pneumocystis carinii*. More particularly, this invention relates to a method for diagnosing for *Pneumocystis carinii* which comprises amplifying a sample of DNA from *Pneumocystis carinii* by polymerase chain reaction (PCR) using species specific primers and detecting the PCR products with species specific radioactive or non-radioactive oligonucleotide probes. This invention also relates to a method for diagnosing for various species of *Pneumocystis carinii* by detecting the presence of a nucleic acid sequence containing the particular 16S or 26S rRNA gene sequence specific for that species of *Pneumocystis carinii*.

12 Claims, 22 Drawing Sheets

FIGURE 2A

```
cgaaagagag gaggtagcac tgTTCCGTAG GTGAACCTGC
GGAAGGATCA TTAatgaaat gttgtcaaga actagtttat    80
ctggttcttg acattttcat cataacactt gtgaacatta
aagatttgct ttgacaggat gggagttagc tttcgtcctg   160
tcagaggttt tcaattaaaa cttttttggt gtttcggtta
aaaatataat ttttaaAAAC TTTCAGCAAT GGATCTCTTG   240
GTTCCCGCGT CGATGAAGAA CGTGGCAAAA TGCGATAAGT
AGTGTGAATT GCAGAATTCA GTGACTCATC GAATTTTTGA   320
ACGCATATTG CGCTCCTCAG TATTCTGTGG AGCATGCCTG
TTTGAGCGTC ATTTttatac ttgaaccttt ttaaggtttg   400
tgttgggcta tgcatttag tattttaca agatgctagt
ctaaaatgga atccagaata ttatttcgtg cagcgtaata   480
gggttaaatt ccaattcgct gttttagaa atgatagact
ggtttgtcta ttgttcctag agagcaattt ttgaacCTTT   560
GACCTCAAAT CAGGTAGGAT TACCCGCTGA ACTTAAGCAT
ATCAATAAGC GGAGGAAAAG AAACTAACAA GGATTCCCTC   640
AGTAACGGCG AGTGAAGTGG GAAAAGCTCA AAATTAAAAT
CTGGCGAGGA TCCTCGTCCG AGTTGTAATT TAGAGAAGTG   720
CTTTTGGCTT GATGCTCTAT TTAAAGTCCT TTGGAACAAG
GCATCATAGA GGGTGATAAT CCCGTACGAG TAGGGTTATT   800
AAGCTATGTA AAAGCACATT CGAAGAGTCG AGTTGTTTGG
GATTGCAGCT CAAAATGGGT GGTAAATTTC ATCTAAAGCT   880
AAATATTAGC GGGAGACCGA TAGCGAACAA GTAGAGTGAT
CGAAAGATGA AAAGAACTTT GAAAAGAGAG TTAAATAGTA   960
CGTGAAATTG CTGAAAGGGA AGCGCTTGCG ATCAGACATG
CCTTATCAGG ATGTTGTTGT CTTGACAATA ACTATTACTT  1040
GGTTTGGCAG GCCAACATCG GTTTCAGCTG CTAGGTAAGT
GTCAAGAGAG GGTAGCCTCT TTCGTGGGGT GGTTAGCTCT  1120
TGGCTTCTGT AGTAGCAGGG ACCGGAAGGT CTAGCGTCAG
CTTGGTTGTT GGCTTAATGG TCTTAAGCGA CCCGTCTTGA  1200
AACACGGACC AAGGAGTCTA ATATCTATGC GAGTGTTTGA
GTGGAAAACT CATACGCGAA ATGAAGTGA AGCAAAAGGT  1280
AGGAACCCTT TAAGGGTGCA CTATCGACCG GTTCAAATTT
ATTGGATTG AGTAAGAGCA TAGCTATTGG GACCCGAAAG  1360
ATGGTGAACT ATGCCTGAAT AGGGTGAAGC CAGAGGAAAC
TCTGGTGGAG GCTCGTAGCG GTTCTGACGT GCAAATCGAT  1440
CGTCAAATTT GGGCATAGGG GCGAAAGACT AATCGAACCA
TCTAGTAGCT GGTTCCTGCC GAAGTTTCCC TCAGGATAGC  1520
AGAAACTCAA TATCAGTTTT ATGAGGTAAA GCGAATGATT
AGAGGCATTG GGGTTGAAAC AACCTTAACC TATTCTCAAA  1600
CTTTAAATAT GTAAGAAGTC CTTGTTGCTT AATTGAACAT
GGACATTAGA ATGAGAGTTT CTAGTGGGCC ATTTTTGGTA  1680
AGCAGAACTG GCGATGCGGG ATGAACCGAA CGCGAGGTTA
AGGTGCCGGA AGCACGCTCA TCAGATACCA CAAAAGGTGT  1760
TAGTTCATCT AGACAGTAGG ACGGTGGCCA TGGAAGTCGG
AATCCGCTAA GGAGTGTGTA ACAACTCACC TACCGAATGA  1840
```

FIGURE 2B

```
ACTGGCCCTG AAAATGGATG GCGCTCAAGC GTGCTACCTA
TACCTCGCCG TCTGGATAA  TGATTCCTAG ACGAGTAGGC 1920
AGGCGTGGGG GTCGTGGCGA AGCCTAGGGC GTGAGCCCGG
GTTGAACGGC CTCTAGTGCA GATCTTGGTG GTAGTAGCAA 2000
ATATTCAAAT GAGGACTTTG AAGACTGAAG TGGGGAAAGG
TTCCATGCGA ACAGTTATTG GGCATGGGTT AGTCGATCCT 2080
AAGAGATAGG GAAACTCCGT TTTAAAGTGC GCGATTTTTC
GCGCCTCTAT CGAAAGGGAA TCCGGTTAAT ATTCCGGAAC 2160
CAGGATATGG ATTCTTCACG GCAACGTAAA TGAAGTCGGA
GACGTCAGCG GGGGGCCTGG GAAGAGTTAT CTTTTCTTCT 2240
TAACAGCCTA TCACCCTGGA ATCGGTTTAT CCGGAGATAG
GGTTCAATGG CTGGTAGAGT TCAGCACTTC TGTTGAATCC 2320
AGTGCGCTTT CGATGACCCT TGAAAATCCG ACGGAAGGAA
TAGTTTTCAT GCCTGGTCGT ACTCATAACC GCAACAGGTC 2400
TCCAAGGTGA ACAGCCTCTA GTTGATAGAA TAATGTAGAT
AAGGGAAGTC GGCAAAATAG ATCCGTAACT TCGGATAAG  2480
GATTGGCTCT AAGGATTGGG TGCATTGGGC TTTAATCGGA
AGCTATTGGA CCAGACGGGA ACTACCTTGG GAAACCGAGG 2560
CGGATCCTGT TAGGATCGAT CAGTGAATGA TTTTAGCAGC
CCTTTGGGCG TCCGATGCAC GCTTAACAAT CAACTTAGAA 2640
CTGGTACGGA CAAGGGGAAT CTGACTGTCT AATTAAAACA
TAGCATTGCG ATGGCCAGAA AGTGGTGTTG ACGCGATGTG 2720
ATTTCTGCCC AGTGCTCTGA ATGTCAAAGT GAAGAAATTC
AACCAAGCGC GGGTAAACGG CGGAGTAAC  TATGACTcac 2800
cttttgaggg tcatgaaagc ggcgcgaaag tgttagctag
tgatccgaaa aataaattcg ggttgcgaca ctgtcaaatt 2880
gcggggagtc cctaaagatt caactactaa gcagcttgtg
gaaacacagt tgtggccgag ttaatagccc tgggtatagt 2960
aacaatgttg aatatgactc ttaattgagg aaatgggtga
tcccagcca  aatcctaagg acatttatt  gtctatggat 3040
gcagttcagc gactagacgg cagtgggtat tgtagagata
tgggttatt  tatggcctta tctacaatgc ttaaggtata 3120
gtctaatctc tttcgaaaga aagagtagtg tgCTCTTAAG
GTAGCCAAAT GCCTCGTCAT CTGATTAGTG ACGCGCATGA 3200
ATGGATTAAC GAGATTCCCA CTGTCCCTAT CTACGATCTA
GCGAAACCAC AGCCAAGGGA ATGGCTTGG  CAAAATCAGC 3280
GGGGAAGAA  GACCCTGTTG AGCTTGACTC TAGTTTGACA
TTGTGAAAAG ACATAGAGGA TGTAGAATAG GTGGGAGCTT 3360
CGGCGCCTGT GAAATACCAC CGCCTTTATT GTTTTTTTAC
TTAATCAGTG GAGCGGGACT GAGCTTTTGC TCATCTTTTA 3440
GCGTTAAGGT CCTTTTACGG GCCGACCCGA GTTGATGACA
TTGTCAGATG GGGAGTTTGG CTGGGCGGC  ACATCTGTCA 3520
AAAGATAACG CAGGTGTCCT AAGGGGAGCT CATTGAGAAC
AGAAATCTCA AGTAGAATAA AAGGGTAAAA GTTCCCTTGA 3600
TTTTGATTTT CAGTACGAAT ACAAACCATG AAAGTGTGGC
CTATCGATCC TCTAAATCCT CGAAATTTGA GGCTAGGGGT 3680
```

FIGURE 2C

```
GCCAGAAAAG TTACCACAGG GATAACTGGC TTGTGGCAGC
CAAGCGTTCA TAGCGACGTT GCTTTTTGAT CCTTCGATGT 3760
CGGCTCTTCC TATCATACCG AAGCAGAATT CGGTAAGCGT
TGGATTGTTC ACCCACTAAT AGGGAACGTG AGCTGGGTTT 3820
AGACCGTCGT GAGACAGGTT AGTTTTACCC TGCTGATGAA
GTTATCGCAA TGGTAATTCA GCTTAGTACG AGAGGAACCG 3900
TTGATTCAGA TATTTGGTTT TTGCGGTTGT CTGACCAGGC
AGTGCCGCGA AGCTATCATC TGTTGGATTA TGGCTGAAAG 4000
CCTCTAAGTC AGAATCCATG CCAGAAAGCG ATGATATTTC
CTCACGTTTT TTGATACAAA TAGGCATCTT GCCAATATCA 4080
GTATTTGGAC GGGTGGAGGC GGACGGAAGT GTTCGTCTCT
GTCCATTAAT ATTAATTAAT ATTCGTGAGG GCGAATCCTT 4160
TGTAGACGAC TTAGTTGAGG AACGGGGTAT TGTAAGCAGT
AGAGTAGCCT TGTTGTTACG ATCTGCTGAG ATTAAGCCtt 4240
tgttcccaag atttgt   4256
```

FIGURE 3

```
Pc  taaAAACTTT  CAGCAATGGA  TCTCTTGGTT  CCCGCGTCGA
Sc  ---.......  ..A...C...  ..........  .T...A....
Tp  AGA.......  ..A.GG....  .A........  ....T.A...
Hs  ---CG...C.  T...GG....  ..A..C..C.  .GT.......

Pc  TGAAGAACGT  GGCA--AAAT  GCGATAAGTA  GTGTGAATTG   75
Sc  .........C  A..G--....  ......C...  A.........   75
Tp  .........C  A..G--....  ......C...  A..C......   78
Hs  .........C  A..GCT.GC.  ....G..T..  A.........   79

Pc  CAGAATTCAG  TGACTCATCG  AATTTTTGAA  CGCATATTGC
Sc  .......C..  ...A......  ...C......  ....C.....
Tp  ......--.C. C..G...A.A  G..C......  A...AG.G.T
Hs  ...G.CA..T  ...-......  .CAC..C...  ....CT.GCG

Pc  GCTCCTCAGT  ATTCTGTGGA  GCATGCCTGT  TTGAGCGTCA  TTT  158
Sc  ..C...TG..  ....CAG..G  ..........  ..........  ...  158
Tp  .GAGG.GTAA  .AA.CT.CAT  .TT..TA.TA  G..T.GCA--  ---  154
Hs  ..C..GGGT.  CC..CCG..G  CT.C......  C........G  C..  159
```

FIGURE 5A

```
Pc CTTTGACCTC AAATCAGGTA GGATTACCCG CTGAACTTAA
Sc G.........  ..........  ...G......  ..........
Tp --C.ACA.CT G.TA..A.C.  A.........  ..........

Pc GCATATCAAT AAGCGGAGGA AAAGAAACTA ACAAGGATTC
Sc .........  ..........  ......C..  ..-C.....G
Tp .......G.  ..........  ..........  ..T.....AG

Pc CCTCAGTAAC GGCGAGTGAA GTGGGAAAAG CTCAAAATTA
Sc ...T......  ..........  .C..C.....  ......T..G
Tp ..C......T ....A....  CA..CT....  ......G.G.

Pc AAATCTGGCG AGGATCCTCG TCCGAGTTGT AATTTAGAGA
Sc ........-T .CCT..GGT. C.........  .....G....
Tp .......AA .---------  -.A..A....  ...C..A...

Pc AGTGCTTTTG GCTTGATGCT CTATTTAAAG TCCTTTGGAA    200
Sc G.GCAAC..T .GGGCCGTTC ..TG.CT.T. .T.C......    198
Tp GT.AACCCAA AGC.A.GCTC ..CGCAT... .T.C......    188

Pc CAAGGCATCA TAGAGGGTGA TAATCCCGTA CGAGTAGGGT
Sc ..G.A.G...  ..........  GC......G  T.GCG...AG
Tp ..G.A.G... A.........  C..C......  GTC.GT.A.G

Pc TATTAAGCTA TGTAAAAGCA CATTCGAAGA GTCGAGTTGT
Sc .GCGGTT..T ...-....TG .C........  ..........
Tp A..GCT.G.G AAGGG...-G .-...A....  ....G.....

Pc TTGGGATTGC AGCTCAAAAT GGGTGGTAAA TTTCATCTAA
Sc ......A...  ....T..G.  ..........  ..C.......
Tp ..........  ...C.T..G. ...A.A...  C...T.....

Pc AGCTAAATAT TAGCGGGAGA CCGATAGCGA ACAAGTAGAG
Sc ..........  .G...A....  ..........  ........C..
Tp ..........  ACA.......  ..........  .......CT.

Pc TGATCGAAAG ATGAAAGAA CTTTGAAAAG AGAGTTAAAT    400
Sc ....G.....  ..........  ..........  ....G...A    397
Tp C..AG.....  ..........  ..........  ..G......-    385

Pc AGTACGTGAA ATTGCTGAAA GGGAAGCGCT TG--------
Sc ..........  ....T.....  ......G..A .T--------
Tp ..-..T....  .CC.T...G. A......TG. A.AAGAGCAA
```

FIGURE 5B

```
Pc CGATCAGACA TGCCTTATCA GG--ATGTTG TTGTCTTGAC
Sc T.........  ..GTG.T.TG T.CCC.C.GC .CC.TG...GG
Tp TA.A.T.GAC G..GCATAAG ..GG.A..GT .AC...ACTG.

Pc AATAACTATT ACTTGGTTTG GCAGGCCAAC A---------
Sc T.GGGGA..C T.GCAT..CA CTG.....G. .---------
Tp GGAGT.G..A CGAAA.G.C. ATGA.TA.GG .AAGGACACA

Pc ---------- TCGGTTTCAG CTGCTAGGTA AGTGTCAAGA
Sc ----------  ..A....TG. TG..AG.A.. .A.CCAT..G
Tp GAACTTCTAC G.C.G.CAGA AGA.A.AA.G ...TCAG.TT

Pc GAGGGTAGCC TCTTTCGTGG GGTGGTTAGC TCTTGGCTTC    571
Sc A.T.TAGCTT G.C.CG..AA .TATTA.... CTG...GAAT    570
Tp ..A..-..T. A.C.GA.ATC ..G...C.AA C.AGAT.AAA    583

Pc TGTAGTAGCA GGGACCGGAA GGTCTAGCGT CAG-CTTGGT
Sc AC.GCC...T .....T.AGG AC.GCGA... A..T.AA..A
Tp A.GGAA.CTT CA...T...C T.AGG..C. A..--GGC.A

Pc TGTTGGCTTA ATGGTCTTAA GCGACCCGTC TTGAAACACG
Sc ..C....A.. .....TA..T ...CG..... ..........
Tp .T...T.AA. ....CT.CT. CT........ ..........

Pc GACCAAGGAG TCTAATATCT ATGCGAGTGT TTGAGTGGA-
Sc ..........  ....CG... .......... ...G...T.-
Tp ..........  ....TC.AT. .A.......A .A.G.....G

Pc AAACTCATAC GCGAAATGAA AGTGAAGCAA AAGGTAGGAA
Sc ....C.....  ...T...... .......-.GT .G.T.G..GC
Tp ....C.G.C.  ......C... .....GTAC. .G.T--.CC.

Pc CCCTTTAAGG GTGCACTATC GACCGGTTCA AATT-TATTT    768
Sc .T.GCA.GA. ......A... .....A.C.T G..G-.C..C    767
Tp AG.CGC.... TA...GC... AC...ACCT. G...C.CCGA    779

Pc GGA-----TT GAGTAAGAGC ATAGCTATTG GGACCCGAAA
Sc ...TGGAT.. .......... ......G... ..........
Tp A..AGGGT.C ...G...... T..AT.G..A ..........

Pc GATGGTGAAC TATGCCTGAA TAGGGTGAAG CCAGAGGAAA
Sc ..........  .......... .......... ..........
Tp ..........  ..C..T.... .......... ....G.....
```

FIGURE 5C

```
Pc CTCTGGTGGA GGCTCGTAGC GGTTCTGACG TGCAAATCGA
Sc .......... .......... .......... ..........
Tp .......... A......... .A.A...... ........T

Pc TCGTCAAATT TGGGCATAGG GGCGAAAGAC TAATCGAACC
Sc .....G.... ....T..... .......... ..........
Tp .......... ..A.TG.... .......... ..........

Pc ATCTAGTAGC TGGTTCCTGC CGAAGTTTCC CTCAGGATAG   963
Sc .......... .......... .......... ..........   967
Tp .......... ......CT.. ........T. ..........   979

Pc CAGAAACTCA ATATCAGTTT TATGAGGTAA AGCGAATGAT
Sc .....G...- G......... .......... ..........
Tp ..AG.G.AAG TACG...... ...T...... ..........

Pc TAGAGGCATT GGGGTTGAAA CAACCTTAAC CTATTCTCAA
Sc ......TTCC .....C.... TG.....G.. ..........
Tp ......AC.C ......CC.. G..T..CG.. ..........

Pc ACTTTAAATA TGTAAGA--A GTCCTTGTTG CTTAATTGAA
Sc .......... .......--. .........A ..........
Tp .........T G......GCC .CGGAGT..T ..........

Pc CATGGACATT AGAATG-AGA GTTTCTAGTG GGCCATTTTT
Sc .G........ T.....A... .C..T..... ..........
Tp .-.CTCGGG. ......C..T .C.CT..... ..........

Pc GGTAAGCAGA ACTGGCGATG CGGGATGAAC CGAACGCGAG   1160
Sc .......... .......... .......... .....TAGA   1164
Tp .......... .......... .A........ .T....TTGA  1175

Pc GTTAAGGTGC CGGAA-GCAC GCTCATCAGA TACCACAAAA
Sc .......... .....TA... .......... C.........
Tp .A.....C.. .CA..T.... .......... ..........

Pc GGTGTTAGTT CATCTAGACA GTAGGACGGT GGCCATGGAA
Sc .......... .......... .CC....... ..........
Tp ......G... ...A.G.... .C........ ....T.....

Pc GTCGGAATCC GCTAAGGAGT GTGTAACAAC TCACCTACCG
Sc .......... .......... .......... .....GG...
Tp ..TA...... .......... .......... ......G...
```

FIGURE 5D

```
Pc AATGAACTGG CCCTGAAAAT GGATGGCGCT CAAGCGTGCT
Sc ........A. .......... .......... ........T.
Tp ........A. .......... ......G... ........T.

Pc ACCTATACCT CGCCGTCTGG GAT--AATGA TTCCTAGACG 1357
Sc ........TC TA.....A.. .T.GAT.... .G..CT.... 1364
Tp G..G....TC AA...A..A.A .CAAATGC.. GG.T.T..T. 1378

Pc AGTAGGCAGG CGTGGGGGTC -GTGGCGAAG CCTAGGGCGT
Sc .......... ....A.... A...A..... ....AC...
Tp ......AG.. ....ATC..T -.CCTA.... TA.T......

Pc GAGCCCGGGT TGAACGGCCT CTAGTGCAGA TCTTGGTGGT
Sc A..GT..... C......... .......... ..........
Tp ....T-ATA  G..G.A...GA T......... ..........

Pc AGTAGCAAAT ATTCAAATGA GGACTTTGAA GACTGAAGTG
Sc .......... .......... .A........ ..........
Tp .......... .......... .A........ ...C......

Pc GGGAAAGGTT CCATGCGAAC AGTTATTGGG CATGGGTTAG
Sc .......... ...C.TC... ..CAG....A .G........
Tp .A...G.... ....A..... ..CA....TT .........C

Pc TCGATCCTAA GAGATAGGGA AACTCCGTTT TA-AAGTGC- 1554
Sc .......... .....G.... .G........ C.-...GC.T 1563
Tp .......... ..C.....TT ......T.GC A.T.CAA.AA 1576

Pc GCGATTTTTC GCGCCTCTAT CGAAAGGGAA TCCGGTTAAT
Sc .ATT..A.G. AG...A.C.. .......... .......-...G
Tp .ACG..C.CG TTTT.GT.G. .A........ .GA.......

Pc ATTCCGGAAC CAGGATATGG ATTCTTCACG GCAACGTAAA
Sc .......... TT........ .......... .T......C
Tp .....TC..G .T...CG... -.ATAGAGT. .T...AC...

Pc TGAAGTCGGA GACGTCAGCG GGGGCCTGG  GAAGAGTTAT
Sc ....TGT... ......G... C.A.C..... ..G.......
Tp GA..CC.... ........A  ...A.C.ACT. ..........

Pc CTTTTCTTCT TAACAGCCTA TCACCCTGGA ATCGGTTTAT
Sc .......... .......T.. .....C.... ..T.......
Tp ........T. .....TA... .GG..A..A. .AT..A....
```

FIGURE 5E

```
Pc  CCGGAGATA- GGGTTCAATG GCTGGTAGAG TTCAGCA-CT 1752
Sc  ........G- ....CTT... .....A.... GC......-.C 1760
Tp  ..A.....T  C...C.GT.C. TA...C.... CAGCT...C.C 1775

Pc  TCTGTTGAAT CCAGTGCGCT TTCGATGACC CTTGAAAATC
Sc  .T..C..GC. ...G....... .GT..C.G.. .G........
Tp  .AA.AGCTG. .AGT....... .CT........ ..........

Pc  CGACGGAAGG AATAGTTTTC ATGCCTGGTC GTACTCATAA
Sc  .ACA...... .......... ....TA.... .....G....
Tp  T.GG...-.. .CATAA.... .C...A.T.. ....C.....

Pc  CCGCAACAGG TCTCCAAGGT GAACAGCCTC TAGTTGATAG
Sc  .....G.... .......... .......... ..........
Tp  .....T.... .......... T.G....... .G..CC....

Pc  AATAATGTAG ATAAGGGAAG TCGGCAAAAT AGATCCGTAA
Sc  .......... .......... .......... ..........
Tp  ..C....... .......... ........T. G.........

Pc  CTTCGGGATA AGGATTGGCT CTAAGGATTG GGTGCATTGG 1952
Sc  .......... .......... ......G.C. ...AGTGA.. 1960
Tp  .......... .......... ..G.....C. ...AT.AA.. 1973

Pc  GCTTTAATCG GAAGCTATTG GACCAGACGG GAACTACCTT
Sc  ..C..GG..A ..C..AGCG. .CGTGCTT.T .G...G.T.G
Tp  C.A...GAT. AT.T.C.AGC TTGTTTGTTA .TGTGG.AAC

Pc  GGGAAAC--- -----CGAGG CGGATCCTGT TAGGATCGAT
Sc  .T.GGG.TTG CTCTG.T... ....CTACT. GC.TGC.TTG
Tp  AT.------- ---------- ----CTGATA G.CTTG...C

Pc  CAGTGAATGA TTTTAGCAGC CCTTTGGGCG TCCGATGCAC
Sc  TT..AG.C.G CC...G.T..G T..C.T.TA. A...TC..TT
Tp  .GAA....TC ..G.G.T..A ...------- -.G.TC.TCT

Pc  GC------TT AACAATCAAC TTAGAACTGG TACGGACAAG
Sc  ..TACAAT.A .CAG...... .......... ..........
Tp  TTATACAA.. ...G...... .C........A AG.......A

Pc  GGGAATCTGA CTGTCTAATT AAAACATAGC ATTGCGATGG 2138
Sc  .......... .......... .......... .......... 2160
Tp  ..T....C.. ....T....A .....A.... ....T..C.. 2144
```

FIGURE 5F

```
Pc CCAGAAAGTG GTGTTGACGC GATGTGATTT CTGCCCAGTG
Sc T.........  A.........  A.........  ..........
Tp ..-TC..CA. ...A....A. A.........  ..........

Pc CTCTGAATGT CAAAGTGAAG AAATTCAACC AAGCGCGGGT
Sc .......... .......... .......... .......A..
Tp .......... .......C.  C......... ..........

Pc AAACGGCGGG AGTAACTATG ACTCTCTTAA GGTAGCCAAA
Sc .......... .......... .......... ..........
Tp .......... .......... .......... ..........

Pc TGCCTCGTCA TCTGATTAGT GACGCGCATG AATGGATTAA
Sc .......... ...A...... .......... ..........
Tp .......... ...A...... .......... ..........

Pc CGAGATTCCC ACTGTCCCTA TCTACGATCT AGCGAAACCA  2338
Sc .......... .......... .....T.... ..........  2360
Tp T.....A..  .......... .....T.... ......C...  2343

Pc CAGCCAAGGG AATGGGCTTG GCAAAATCAG CGGGGAAAGA
Sc .......... ..C....... ...G...... ..........
Tp ....T..... ..C...... ..A .A.T...... ..........

Pc AGACCCTGTT GAGCTTGACT CTAGTTTGAC ATTGTGAAAA
Sc .......... .......... .......... ........G.
Tp .......... .......... .....C.A.. T........T

Pc GACATAGAGG ATGTAGAATA GGTGGGAGCT TCGGCGCCTG
Sc .......... G......... A......... ........A.
Tp .G..CGTG.. G.A...CC.. ........AG AAAT..AGCC

Pc TGAAATACCA CCGCCTTTAT TGTTTTTTTA CTTAATCAGT
Sc .......... .TA....... A....C.... ....T...A.
Tp ..T..A.... .TA..CACG. A..CA....G ....T.TC..

Pc GGAGCGGGAC TGAGCTT--T TGCTCATCTT TTAGCGTT-A  2535
Sc .A.....AG. ..GAA..CA. .TTC..CG.. C....A..C.  2560
Tp .A.------A AA.AAC.GG. GAGAACCAG. .CTAAAA.T.  2538

Pc AGGTCCTTTT ACGGGCCGAC CCGAGTTGAT GACATTGTCA
Sc ......CA.. CG....T..T ...G.....A ..........
Tp ...A.A...A TT.TCTGATT TTTGCGAA.A .....G..T.
```

FIGURE 5G

```
Pc GATGGGGAGT TTGGCTGGGG CGGCACATCT GTCAAAAGAT
Sc .G........ .......... .......... ..T...C...
Tp .GG....... ...T...... ...A.TGC.. ..T...CC..

Pc AACGCAGGTG TCCTAAGGGG AGCTCATTGA GAACAGAAAT
Sc .......A.. .......... G......G.. ..........
Tp ......C. ......T.T ......G... ....G.....

Pc CTCAAGTAGA ATAAAAGGGT AAAAGTTCCC TTGATTTTGA
Sc ...C...... .C........ ...---G... C.T.G.....
Tp ....C..... .C........ .....C.A.A ..........

Pc TTTTCAGTAC GAATACAAAC CA-TGAAAGT GTGGCCTATC 2734
Sc -......GT. .......... ..T....... .......... 2756
Tp ........T. .......... .G-C.....C .......... 2737

Pc GATCCTCTAA ATCCTCGAAA TTTGAGGCTA GGGGTGCCAG
Sc .....T..G  TC.....G.. .......... .A........
Tp ......T... -CTT.AC..G ...T.A.... .A....T...

Pc AAAAGTTACC ACAGGGATAA CTGGCTTGTG GCAGCCAAGC
Sc .......... .......... .......... ....T.....
Tp .......... .......... .......... .........A

Pc GTTCATAGCG ACGTTGCTTT TTGATCCTTC GATGTCGGCT
Sc .......... ...A...... .....T.... ..........
Tp ......T... .......... .......... ..........

Pc CTTCCTATCA TACCGAAGCA GAATTCGGTA AGCGTTGGAT
Sc .......... .......... .......... ..........
Tp .......... .TGT...... .......ACA. C.T..C....

Pc TGTTCACCCA CTAATAGGGA ACGTGAGCTG GGTTTAGACC 2934
Sc .......... .......... ...A...... .......... 2956
Tp .......G.. .......... .......... .......... 2936

Pc GTCGTGAGAC AGGTTAGTTT TACCCTGCTG ATGAAGTTAT
Sc .......... .......... .....A.... .....TG.TA
Tp .......... .......... .....A.... .....ACG..

Pc C--GCAATGG TAATTCAGCT TAGTACGAGA GGAACCGTTG
Sc .CA....A.. .....G.A.. .......... .....A...C
Tp GTT..G.CA. .....T.AG. .......... ......C..A
```

FIGURE 5H

```
Pc ATTCAGATAT TTGGTTTTTG CGGTTGTCTG ACCAGGCAGT
Sc ....G....A .......... ...C..... .T......T.
Tp .A.......A ....AAA.A .......... .AA..A..A.

Pc GCCGCGAAGC TATCATCTGT TGGATTATGG CTGAAAGCCT
Sc .......... -.C....C.C .......... .....C....
Tp ....T..... ..C....... .........A .....G....

Pc CTAAGTCAGA ATCCATGCCA GAAAGCGATG ATATTT----   3128
Sc .......... ........T. ...C...G.. ...T.C.TTGC 3155
Tp .......... ........TG ......A... TCTAAGTGTG  3136

Pc ----CCTCAC GTTTTTTGAT ACAAAT-AGG CATCTT----
Sc TCCA.ACA.T A.AGA.G... ..G...A... .G..C.TGTG
Tp ATGATAAACG AAAAAAAATA .G....---- ----------

Pc --------G CCAATATCAG TATTTGGACG GGTGGAGGCG
Sc GCGTCGCTGA A.C...G... GC.AGCA... .TGCACTTG.
Tp ---------- ----..AGTT CGAAA..TA. A.C....AA.

Pc GACGGAAGTG TTCGTCTCTG TCCATTAATA TTAATT---A
Sc CGGAA.G.CC ..G.GTG..T G.TGGCG.AT .GC.A.GTC.
Tp AG..A..AA. C.T.ATCT.A A.TGC....C G.....CCA.

Pc ATATTCGTGA GGGCGAATCC TTTGTAGACG ACTTAGTTGA
Sc T.T.G....G ..ATA....A ......T... ......A...T
Tp ..TA..A.CT AC.TA....T .......... .....A.--.

Pc GGAACGGGGT ATTGTAAGCA GTAGAGTAGC CTTGTTGTTA   3307
Sc AC........ .......G.. .......... ..........   3355
Tp C.G.AC.... .......T.. TG......A  A.--A.TC..   3304

Pc CGATCTGCTG AGATTAAGCC tttgttccca agatttgt     3345
Sc .......... .......... ......GT.T -.......    3392
Tp .......... .....C.... CG.C.C.TT. -.....A.    3341
```

FIGURE 6B

```
                          313
      G A U          G
   U       CCUAUG
 G               | | | | · |
  G             GGAUGC
   G G                    U
      A-U                  UAAGAUA
      U-A      P8               352
      A-U
      U-A
    A    U
     U A
```

FIGURE 7A

```
Pc1  GGTTTGGCAG GCCAACA--- ---------- ------TCGG  505
Pc2  .......... .......--- ---------- ------....
Sc   AT..CACTG. .....G..-- ---------- -------.A.
Tp   A.G.C.ATGA .TA.GG..AAG GACACAGAAC TTCTACG.C.

Pc1  TTTCAGCTGC TAGGTAAGTG TCAAGAGAGG GTAGCCTCTT  545
Pc2  .......... .......AGA ........A. ..........
Sc   ...TG.TG.. AG.A...A.C CAT..GA.T. TAGCTTG.C.
Tp   G.CAGAAGA. A.AA.G...T CAG.TT...A. .-..T.A.C.

Pc1  TCGTGGGGTG GTTAGCTCTT GGCTTCTGTA GTAGCAGGGA  585
Pc2  .TT....... T......... .AT.GTA... .C...T....
Sc   CG..AA.TAT TA....CTG. ...GAATAC.G CC...T....
Tp   GA.ATC..G. ...C.AAC.AG AT.AAAA.GG AA.CTTCA..

Pc1  CCGGAAGGTC TAGCGTC--- -AG-CTTGGT TGTTGGCTTA  620
Pc2  .......... ....AAAATA T..-...... ..........
Sc   .T.AGGAC.G CGA...A--- -...T.AA..A ..C....A..
Tp   .T...CT.AG GG..C.A--- -.--GGC.A .T...T.AA.

Pc1  ATGGTCTTAA GCGACCCGTC TTGAAACACG GACCAAGGAG  660
Pc2  .......... .......... .......... ..........
Sc   .....TA..T ..CG...... .......... ..........
Tp   ....CT.CT. CT........ .......... ..........

Pc1  TCTAATATCT ATGCGAGTGT TTGAGTGGA- AAACTCATAC  699
Pc2  .......... .......... ...G.....- ....C...G.
Sc   .....CG... .......... ...G...T.- ....C.....
Tp   ....TC.AT. .A.......A .A.G.....G ....C.G.C.

Pc1  GCGAAATGAA AGTGAAGCAA AAGGTAGGAA CCCTTTAAGG  739
Pc2  .......... .......... .-...G.... .....C-G..
Sc   ...T...... .......-.GT .G.T.G..GC .T.GCA.GA.
Tp   ......C... .....GTAC. .-...GCC.. G..G-C....
```

FIGURE 7B

```
Pc1  GTGCACTATC GACCGGTTCA AATT-TATTT GGA-----TT  773
Pc2  .....C.... .......... ....-..... ........C
Sc   .....A.... .....A.C.T G..G-.C..C ...TGGAT..
Tp   TA...GC... AC...ACCT. G...C.CCGA A..AGGGT.C

Pc1  GAGTAAGAGC ATAGCTATTG GGACCCGAAA GATGGTGAAC  813
Pc2  .....G.... .......... .......... ..........
Sc   .......... ......G... .......... ..........
Tp   ...G...... T..AT.G..A .......... ..........

Pc1  TATGCCTGAA TAGGGTGAAG CCAGAGGAAA CTCTGGTGGA  853
Pc2  .......... .......... .......... ..........
Sc   .......... .......... .......... ..........
Tp   ..C..T.... .......... ....G..... ..........

Pc1  GGCTCGTAGC GGTTCTGACG TGCAAATCGA TCGTCAAATT  893
Pc2  .......... .......... .......... ..........
Sc   .......... .......... .......... .....G....
Tp   A......... .A.A...... .........T ..........

Pc1  TGGGCATAGG GGCGAAAGAC TAATCGAACC ATCTAGTAGC  933
Pc2  .......... .......... .......... ..........
Sc   ....T..... .......... .......... ..........
Tp   ..A.TG.... .......... .......... ..........

Pc1  TGGTTCCTGC CGAAGTTTCC CTCAGGATAG C   964
Pc2  .......... .......... .......... .
Sc   .......... .......... .......... .
Tp   .......CT. .........T .......... .
```

FIGURE 8A

```
Pc1  GGGAACGTGA GCTGGGTTTA GACCGTCGTG AGACAGGTTA  2950
Pc2  .......... .......... .......... ..........
Sc   ......A... .......... .......... ..........
Tp   .......... .......... .......... ..........

Pc1  GTTTTACCCT GCTGATGAAG TTATC--GCA ATGGTAATTC  2988
Pc2  .......... .......... .....--... ..........
Sc   .......... A........T G.TA.CA... ...A......G
Tp   .......... A........A CG..GTT..G .CA.......T

Pc1  AGCTTAGTAC GAGAGGAACC GTTGATTCAG ATATTTGGTT  3028
Pc2  .A........ .......... .......... ..........
Sc   .A........ .........A ...C....G. ...A......
Tp   .AG....... .......... C..A.A.... ...A.....A

Pc1  TTTGCGGTTG TCTGACCAGG CAGTGCCGCG AAGCTATCAT  3068
Pc2  .......... .......... .......... ..........
Sc   ......C... .....T.... ..T....... .....-.C...
Tp   AA.A...... ....AA..A ..A.....T. ......C...

Pc1  CTGTTGGATT ATGGCTGAAA GCCTCTAAGT CAGAATCCAT  3108
Pc2  .......... ........C. .......... ..........
Sc   .C.C...... ........C. .......... ..........
Tp   .......... ...A.....G .......... ..........

Pc1  GCCAGAAAGC GATGAT--AT TTCCTCAC-G TTTTTTGATA  3145
Pc2  .......... .....AA.. ........AC A.........
Sc   ..T....C.. .G....TTC. ...G...-.AC ACAA.AT.G.
Tp   ..TG...... A...------ --T..A.GT. .GA.GAT.A.

Pc1  CAAATAGGCA TCTTGC---- ---------- ---CAATATC  3168
Pc2  T.G....... .T....---- ---------- ---..G....
Sc   TGG...C.A. .AAG..GTCC TTGTGGCGTC GCTG..CCAT
Tp   .G..A.AAA. .AA------ ---------- ---G..AT.A

Pc1  AG--TATTTG GACGGGTGGA GGCGGACGGA AGTGTTCGTC  3206
Pc2  ..TA...... ........G ....A..... ..........
Sc   ..CAGGC.A. C.AC....C. CTT..CG.A. ..GCC.T.GG
Tp   ..TTCGAAA. .TA.A.C... .AA.AG..A. .AA.C.T.-A
```

FIGURE 8B

```
Pc1  TCTGTCCATT A--ATATTAA --TTAATATT CGTGAGGGCG  3242
Pc2  .......... .AC...A..T --AA.....G ........T.
Sc   .GCT.G.TGG CGA..TGC.. TG.C.T.T.G ....G..ATA
Tp   ...TAA.TGC TAATCG.A.T TCCA...TA. .A.CTAC.TA

Pc1  AATCCTTTGT AGACGACTTA GTTGAGGAAC GGGGTATTGT  3282
Pc2  .......... .......... .......... ......C...
Sc   ....A..... .T........ .A..TAC... ..........
Tp   ....T..... .......... A.--.C.G.A C.........

Pc1  AAGCAGTAGA GTAGCCTTGT TGTTACGATC TGCTGAGATT  3322
Pc2  .......... .......... .......... ..........
Sc   ....G..... .......... .......... ..........
Tp   ...T.TG... ....AA.--A .TC....... ..........

Pc1  AAGCC  3327
Pc2  .....
Sc   .....
Tp   C....
```

FIGURE 10

```
TCAAAAAGAA CATTTCTTCT GAGTGGTGAG GGGTCCGTTA
GAGCACACTC GCTCCTTGGA AGAGATGTTT TTTTTGATAT    80
TAGGAACCAA TAGAATATTT AGAATTTAAT TTAGATTAAA
TTATAGAAGG GTATCTGTAG CGATAAGTTT CCATTTCAAA   160
TTTTTCTGAT GCAGTAGTAT GTTCTTTTCT AAAATAAAAT
GATAGTTTAT TAATGATTAA ACTAATTATT ATCCTTTGGC   240
CATCTTTTTC TACATTTTCC AGAAACAGAT CTAATTACGT
TTTTGCTATC TATAATTATT AAAAATAATC ATATATCTTT   320
AAAGTTGACC TCAACGTCTT AAAATGTTTA GTTTTTTAAT
TAACCCTAAA CCCTAGAACA C                       381
```

5,776,680

SEQUENCE LISTING ( 1 ) GENERAL INFORMATION:

( i i i ) NUMBER OF SEQUENCES: 32

( 2 ) INFORMATION FOR SEQ ID NO:1:

( i ) SEQUENCE CHARACTERISTICS:
        ( A ) LENGTH: 18 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:1:

AACAGCTATG ACCATGAT     18

( 2 ) INFORMATION FOR SEQ ID NO:2:

( i ) SEQUENCE CHARACTERISTICS:
        ( A ) LENGTH: 18 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:2:

TTCCCAGTCA CGACGTTG     18

( 2 ) INFORMATION FOR SEQ ID NO:3:

( i ) SEQUENCE CHARACTERISTICS:
        ( A ) LENGTH: 18 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:3:

TGTAAAACGA CGGCCAGT     18

( 2 ) INFORMATION FOR SEQ ID NO:4:

( i ) SEQUENCE CHARACTERISTICS:
        ( A ) LENGTH: 27 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:4:

AGGGATTGGT TGGCCTGGTC CTCCGAA     27

( 2 ) INFORMATION FOR SEQ ID NO:5:

( i ) SEQUENCE CHARACTERISTICS:
        ( A ) LENGTH: 22 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:5:

```
CTTTCCAGTA ATAGGCTTAT CG                                                        22
```

( 2 ) INFORMATION FOR SEQ ID NO:6:

( i ) SEQUENCE CHARACTERISTICS:
        ( A ) LENGTH: 22 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:6:

```
GCTATCCTGA GGGAAACTTC GG                                                        22
```

( 2 ) INFORMATION FOR SEQ ID NO:7:

( i ) SEQUENCE CHARACTERISTICS:
        ( A ) LENGTH: 24 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:7:

```
CCCGTCTTGA AACACGGACC AAGG                                                      24
```

( 2 ) INFORMATION FOR SEQ ID NO:8:

( i ) SEQUENCE CHARACTERISTICS:
        ( A ) LENGTH: 26 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:8:

```
CCCGCGATCA GCAAAAGCTA ATCTGG                                                    26
```

( 2 ) INFORMATION FOR SEQ ID NO:9:

( i ) SEQUENCE CHARACTERISTICS:
        ( A ) LENGTH: 26 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:9:

```
CCATACAGAA GACCATTCTT TATCCC                                                    26
```

( 2 ) INFORMATION FOR SEQ ID NO:10:

( i ) SEQUENCE CHARACTERISTICS:
        ( A ) LENGTH: 20 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:10:

```
GGCCGATCAA ACTCTCTTCC                                                           20
```

( 2 ) INFORMATION FOR SEQ ID NO:11:

( i ) SEQUENCE CHARACTERISTICS:
                    ( A ) LENGTH: 21 base pairs
                    ( B ) TYPE: nucleic acid
                    ( C ) STRANDEDNESS: unknown
                    ( D ) TOPOLOGY: unknown ( i i ) MOLECULE TYPE: DNA (genomic)

( x i ) SEQUENCE DESCRIPTION: SEQ ID NO:11:

GGGAAAAGGT CGTGGGGAGC G                                                              21

( 2 ) INFORMATION FOR SEQ ID NO:12:

( i ) SEQUENCE CHARACTERISTICS:
                    ( A ) LENGTH: 21 base pairs
                    ( B ) TYPE: nucleic acid
                    ( C ) STRANDEDNESS: unknown
                    ( D ) TOPOLOGY: unknown ( i i ) MOLECULE TYPE: DNA (genomic)

( x i ) SEQUENCE DESCRIPTION: SEQ ID NO:12:

GGGGAAGACC GCCCTGATAG G                                                              21

( 2 ) INFORMATION FOR SEQ ID NO:13:

( i ) SEQUENCE CHARACTERISTICS:
                    ( A ) LENGTH: 26 base pairs
                    ( B ) TYPE: nucleic acid
                    ( C ) STRANDEDNESS: unknown
                    ( D ) TOPOLOGY: unknown ( i i ) MOLECULE TYPE: DNA (genomic)

( x i ) SEQUENCE DESCRIPTION: SEQ ID NO:13:

GAGCCAATCC TTATCCCGAA GTTACG                                                         26

( 2 ) INFORMATION FOR SEQ ID NO:14:

( i ) SEQUENCE CHARACTERISTICS:
                    ( A ) LENGTH: 23 base pairs
                    ( B ) TYPE: nucleic acid
                    ( C ) STRANDEDNESS: unknown
                    ( D ) TOPOLOGY: unknown ( i i ) MOLECULE TYPE: DNA (genomic)

( x i ) SEQUENCE DESCRIPTION: SEQ ID NO:14:

GTCTAAACCC AGCTCACGTT CCC                                                            23

( 2 ) INFORMATION FOR SEQ ID NO:15:

( i ) SEQUENCE CHARACTERISTICS:
                    ( A ) LENGTH: 19 base pairs
                    ( B ) TYPE: nucleic acid
                    ( C ) STRANDEDNESS: unknown
                    ( D ) TOPOLOGY: unknown ( i i ) MOLECULE TYPE: DNA (genomic)

( x i ) SEQUENCE DESCRIPTION: SEQ ID NO:15:

GGGTGGTGGT GCATGGCCG                                                                 19

( 2 ) INFORMATION FOR SEQ ID NO:16:

( i ) SEQUENCE CHARACTERISTICS:
                    ( A ) LENGTH: 22 base pairs
                    ( B ) TYPE: nucleic acid
                    ( C ) STRANDEDNESS: unknown
                    ( D ) TOPOLOGY: unknown ( i i ) MOLECULE TYPE: DNA (genomic)

( x i ) SEQUENCE DESCRIPTION: SEQ ID NO:16:

CCTTCCGCAG GTTCACCTAC GG    22

( 2 ) INFORMATION FOR SEQ ID NO:17:

( i ) SEQUENCE CHARACTERISTICS:
        ( A ) LENGTH: 18 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:17:

CCGCAGCAGG TCTCCAAG    18

( 2 ) INFORMATION FOR SEQ ID NO:18:

( i ) SEQUENCE CHARACTERISTICS:
        ( A ) LENGTH: 21 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:18:

CGAAAGAGAG GAGGTAGCAC C    21

( 2 ) INFORMATION FOR SEQ ID NO:19:

( i ) SEQUENCE CHARACTERISTICS:
        ( A ) LENGTH: 20 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:19:

GGTCCGTGTT TCAAGACGGG    20

( 2 ) INFORMATION FOR SEQ ID NO:20:

( i ) SEQUENCE CHARACTERISTICS:
        ( A ) LENGTH: 21 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:20:

GGGAACGTGA GCTGGGTTTA G    21

( 2 ) INFORMATION FOR SEQ ID NO:21:

( i ) SEQUENCE CHARACTERISTICS:
        ( A ) LENGTH: 21 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:21:

GGTTTGGCAG GCCAACATCG G    21

(2) INFORMATION FOR SEQ ID NO:22:

(i) SEQUENCE CHARACTERISTICS:
        (A) LENGTH: 21 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:22:

CCATGAAAGT GTGGCCTATC G    21

(2) INFORMATION FOR SEQ ID NO:23:

(i) SEQUENCE CHARACTERISTICS:
        (A) LENGTH: 18 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:23:

GCCTGGTCAG ACAACCGC    18

(2) INFORMATION FOR SEQ ID NO:24:

(i) SEQUENCE CHARACTERISTICS:
        (A) LENGTH: 18 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:24:

GGATTATGGC TGAACGCC    18

(2) INFORMATION FOR SEQ ID NO:25:

(i) SEQUENCE CHARACTERISTICS:
        (A) LENGTH: 20 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:25:

GGCTTAATCT CAGCAGATCG    20

(2) INFORMATION FOR SEQ ID NO:26:

(i) SEQUENCE CHARACTERISTICS:
        (A) LENGTH: 19 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:26:

GACGAGGCAT TTGGCTACC    19

(2) INFORMATION FOR SEQ ID NO:27:

( i ) SEQUENCE CHARACTERISTICS:
            ( A ) LENGTH: 18 base pairs
            ( B ) TYPE: nucleic acid
            ( C ) STRANDEDNESS: unknown
            ( D ) TOPOLOGY: unknown ( i i ) MOLECULE TYPE: DNA (genomic)

( x i ) SEQUENCE DESCRIPTION: SEQ ID NO:27:

GTACACACCG CCCGTCGC                                                              18

( 2 ) INFORMATION FOR SEQ ID NO:28:

( i ) SEQUENCE CHARACTERISTICS:
            ( A ) LENGTH: 18 base pairs
            ( B ) TYPE: nucleic acid
            ( C ) STRANDEDNESS: unknown
            ( D ) TOPOLOGY: unknown ( i i ) MOLECULE TYPE: DNA (genomic)

( x i ) SEQUENCE DESCRIPTION: SEQ ID NO:28:

TTTAGCTCTT GATTGTAG                                                              18

( 2 ) INFORMATION FOR SEQ ID NO:29:

( i ) SEQUENCE CHARACTERISTICS:
            ( A ) LENGTH: 18 base pairs
            ( B ) TYPE: nucleic acid
            ( C ) STRANDEDNESS: unknown
            ( D ) TOPOLOGY: unknown ( i i ) MOLECULE TYPE: DNA (genomic)

( x i ) SEQUENCE DESCRIPTION: SEQ ID NO:29:

CGCATATTTT ATATTATG                                                              18

( 2 ) INFORMATION FOR SEQ ID NO:30:

( i ) SEQUENCE CHARACTERISTICS:
            ( A ) LENGTH: 18 base pairs
            ( B ) TYPE: nucleic acid
            ( C ) STRANDEDNESS: unknown
            ( D ) TOPOLOGY: unknown ( i i ) MOLECULE TYPE: DNA (genomic)

( x i ) SEQUENCE DESCRIPTION: SEQ ID NO:30:

GTTAGCTCTT GGCTTCTG                                                              18

( 2 ) INFORMATION FOR SEQ ID NO:31:

( i ) SEQUENCE CHARACTERISTICS:
            ( A ) LENGTH: 4256 base pairs
            ( B ) TYPE: nucleic acid
            ( C ) STRANDEDNESS: unknown
            ( D ) TOPOLOGY: unknown ( i i ) MOLECULE TYPE: DNA (genomic)

( x i ) SEQUENCE DESCRIPTION: SEQ ID NO:31:

CGAAAGAGAG GAGGTAGCAC CGTTCCGTAG GTGAACCTGC GGAAGGATCA TTAATGAAAT    60
GTTGTCAAGA ACTAGTTTAT CTGGTTCTTG ACATTTTCAT CATAACACTT GTGAACATTA    120
AAGATTTGCT TTGACAGGAT GGGAGTTAGC TTTCGTCCTG TCAGAGGTTT TCAATTAAAA    180
CTTTTTTGGT GTTTCGGTTA AAAATATAAT TTTTAAAAAC TTTCAGCAAT GGATCTCTTG    240
GTTCCGCGT CGATGAAGAA CGTGGCAAAA TGCGATAAGT AGTGTGAATT GCAGAATTCA    300

| | | | | | |
|---|---|---|---|---|---|
| GTGACTCATC | GAATTTTTGA | ACGCATATTG | CGCTCCTCAG | TATTCTGTGG | AGCATGCCTG | 360 |
| TTTGAGCGTC | ATTTTTATAC | TTGAACCTTT | TTAAGGTTTG | TGTTGGGCTA | TGCATTTTAG | 420 |
| TATTTTTACA | AGATGCTAGT | CTAAAATGGA | ATCCAGAATA | TTATTTCGTG | CAGCGTAATA | 480 |
| GGGTTAAATT | CCAATTCGCT | GTTTTTAGAA | ATGATAGACT | GGTTTGTCTA | TTGTTCCTAG | 540 |
| AGAGCAATTT | TTGAACCTTT | GACCTCAAAT | CAGGTAGGAT | TACCCGCTGA | ACTTAAGCAT | 600 |
| ATCAATAAGC | GGAGGAAAAG | AAACTAACAA | GGATTCCCTC | AGTAACGGCG | AGTGAAGTGG | 660 |
| GAAAAGCTCA | AAATTAAAAT | CTGGCGAGGA | TCCTCGTCCG | AGTTGTAATT | TAGAGAAGTG | 720 |
| CTTTTGGCTT | GATGCTCTAT | TTAAAGTCCT | TTGGAACAAG | GCATCATAGA | GGGTGATAAT | 780 |
| CCCGTACGAG | TAGGGTTATT | AAGCTATGTA | AAGCACATT | CGAAGAGTCG | AGTTGTTTGG | 840 |
| GATTGCAGCT | CAAAATGGGT | GGTAAATTTC | ATCTAAAGCT | AAATATTAGC | GGGAGACCGA | 900 |
| TAGCGAACAA | GTAGAGTGAT | CGAAAGATGA | AAGAACTTT | GAAAGAGAG | TTAAATAGTA | 960 |
| CGTGAAATTG | CTGAAAGGGA | AGCGCTTGCG | ATCAGACATG | CCTTATCAGG | ATGTTGTTGT | 1020 |
| CTTGACAATA | ACTATTACTT | GGTTTGGCAG | GCCAACATCG | GTTCAGCTG | CTAGGTAAGT | 1080 |
| GTCAAGAGAG | GGTAGCCTCT | TTCGTGGGGT | GGTTAGCTCT | TGGCTTCTGT | AGTAGCAGGG | 1140 |
| ACCGGAAGGT | CTAGCGTCAG | CTTGGTTGTT | GGCTTAATGG | TCTTAAGCGA | CCCGTCTTGA | 1200 |
| AACACGGACC | AAGGAGTCTA | ATATCTATGC | GAGTGTTTGA | GTGGAAAACT | CATACGCGAA | 1260 |
| ATGAAAGTGA | AGCAAAAGGT | AGGAACCCTT | TAAGGGTGCA | CTATCGACCG | GTTCAAATTT | 1320 |
| ATTTGGATTG | AGTAAGAGCA | TAGCTATTGG | GACCCGAAAG | ATGGTGAACT | ATGCCTGAAT | 1380 |
| AGGGTGAAGC | CAGAGGAAAC | TCTGGTGGAG | GCTCGTAGCG | GTTCTGACGT | GCAAATCGAT | 1440 |
| CGTCAAATTT | GGGCATAGGG | GCGAAAGACT | AATCGAACCA | TCTAGTAGCT | GGTTCCTGCC | 1500 |
| GAAGTTTCCC | TCAGGATAGC | AGAAACTCAA | TATCAGTTTT | ATGAGGTAAA | GCGAATGATT | 1560 |
| AGAGGCATTG | GGGTTGAAAC | AACCTTAACC | TATTCTCAAA | CTTTAAATAT | GTAAGAAGTC | 1620 |
| CTTGTTGCTT | AATTGAACAT | GGACATTAGA | ATGAGAGTTT | CTAGTGGGCC | ATTTTGGTA | 1680 |
| AGCAGAACTG | GCGATGCGGG | ATGAACCGAA | CGCGAGGTTA | AGGTGCCGGA | AGCACGCTCA | 1740 |
| TCAGATACCA | CAAAAGGTGT | TAGTTCATCT | AGACAGTAGG | ACGGTGGCCA | TGGAAGTCGG | 1800 |
| AATCCGCTAA | GGAGTGTGTA | ACAACTCACC | TACCGAATGA | ACTGGCCCTG | AAAATGGATG | 1860 |
| GCGCTCAAGC | GTGCTACCTA | TACCTCGCCG | TCTGGGATAA | TGATTCCTAG | ACGAGTAGGC | 1920 |
| AGGCGTGGGG | GTCGTGGCGA | AGCCTAGGGC | GTGAGCCCGG | GTTAACGGC | CTCTAGTGCA | 1980 |
| GATCTTGGTG | GTAGTAGCAA | ATATTCAAAT | GAGGACTTTG | AAGACTGAAG | TGGGGAAAGG | 2040 |
| TTCCATGCGA | ACAGTTATTG | GGCATGGGTT | AGTCGATCCT | AAGAGATAGG | GAAACTCCGT | 2100 |
| TTTAAAGTGC | GCGATTTTTC | GCGCCTCTAT | CGAAAGGGAA | TCCGGTTAAT | ATTCCGGAAC | 2160 |
| CAGGATATGG | ATTCTTCACG | GCAACGTAAA | TGAAGTCGGA | GACGTCAGCG | GGGGCCTGG | 2220 |
| GAAGAGTTAT | CTTTTCTTCT | TAACAGCCTA | TCACCCTGGA | ATCGGTTTAT | CCGGAGATAG | 2280 |
| GGTTCAATGG | CTGGTAGAGT | TCAGCACTTC | TGTTGAATCC | AGTGCGCTTT | CGATGACCCT | 2340 |
| TGAAAATCCG | ACGGAAGGAA | TAGTTTTCAT | GCCTGGTCGT | ACTCATAACC | GCAACAGGTC | 2400 |
| TCCAAGGTGA | ACAGCCTCTA | GTTGATAGAA | TAATGTAGAT | AAGGGAAGTC | GGCAAAATAG | 2460 |
| ATCCGTAACT | TCGGGATAAG | GATTGGCTCT | AAGGATTGGG | TGCATTGGGC | TTTAATCGGA | 2520 |
| AGCTATTGGA | CCAGACGGGA | ACTACCTTGG | GAAACCGAGG | CGGATCCTGT | TAGGATCGAT | 2580 |
| CAGTGAATGA | TTTTAGCAGC | CCTTTGGGCG | TCCGATGCAC | GCTTAACAAT | CAACTTAGAA | 2640 |
| CTGGTACGGA | CAAGGGGAAT | CTGACTGTCT | AATTAAAACA | TAGCATTGCG | ATGGCCAGAA | 2700 |

```
AGTGGTGTTG ACGCGATGTG ATTTCTGCCC AGTGCTCTGA ATGTCAAAGT GAAGAAATTC    2760
AACCAAGCGC GGGTAAACGG CGGGAGTAAC TATGACTCAC CTTTTGAGGG TCATGAAAGC    2820
GGCGCGAAAG TGTTAGCTAG TGATCCGAAA AATAAATTCG GGTTGCGACA CTGTCAAATT    2880
GCGGGGAGTC CCTAAAGATT CAACTACTAA GCAGCTTGTG GAAACACAGT TGTGGCCGAG    2940
TTAATAGCCC TGGGTATAGT AACAATGTTG AATATGACTC TTAATTGAGG AAATGGGTGA    3000
TCCGCAGCCA AATCCTAAGG ACATTTATT  GTCTATGGAT GCAGTTCAGC GACTAGACGG    3060
CAGTGGGTAT TGTAGAGATA TGGGGTTATT TATGGCCTTA TCTACAATGC TTAAGGTATA    3120
GTCTAATCTC TTTCGAAAGA AAGAGTAGTG TGCTCTTAAG GTAGCCAAAT GCCTCGTCAT    3180
CTGATTAGTG ACGCGCATGA ATGGATTAAC GAGATTCCCA CTGTCCCTAT CTACGATCTA    3240
GCGAAACCAC AGCCAAGGGA ATGGGCTTGG CAAAATCAGC GGGGAAAGAA GACCCTGTTG    3300
AGCTTGACTC TAGTTTGACA TTGTGAAAAG ACATAGAGGA TGTAGAATAG GTGGGAGCTT    3360
CGGCGCCTGT GAAATACCAC CGCCTTTATT GTTTTTTTAC TTAATCAGTG GAGCGGGACT    3420
GAGCTTTTGC TCATCTTTTA GCGTTAAGGT CCTTTTACGG GCCGACCCGA GTTGATGACA    3480
TTGTCAGATG GGGAGTTTGG CTGGGGCGGC ACATCTGTCA AAAGATAACG CAGGTGTCCT    3540
AAGGGGAGCT CATTGAGAAC AGAAATCTCA AGTAGAATAA AAGGGTAAAA GTTCCCTTGA    3600
TTTTGATTTT CAGTACGAAT ACAAACCATG AAAGTGTGGC CTATCGATCC TCTAAATCCT    3660
CGAAATTTGA GGCTAGGGGT GCCAGAAAAG TTACCACAGG GATAACTGGC TTGTGGCAGC    3720
CAAGCGTTCA TAGCGACGTT GCTTTTGAT  CCTTCGATGT CGGCTCTTCC TATCATACCG    3780
AAGCAGAATT CGGTAAGCGT TGGATTGTTC ACCCACTAAT AGGGAACGTG AGCTGGGTTT    3840
AGACCGTCGT GAGACAGGTT AGTTTACCC  TGCTGATGAA GTTATCGCAA TGGTAATTCA    3900
GCTTAGTACG AGAGGAACCG TTGATTCAGA TATTTGGTTT TTGCGGTTGT CTGACCAGGC    3960
AGTGCCGCGA AGCTATCATC TGTTGGATTA TGGCTGAAAG CCTCTAAGTC AGAATCCATG    4020
CCAGAAAGCG ATGATATTTC CTCACGTTTT TTGATACAAA TAGGCATCTT GCCAATATCA    4080
GTATTTGGAC GGGTGGAGGC GGACGGAAGT GTTCGTCTCT GTCCATTAAT ATTAATTAAT    4140
ATTCGTGAGG GCGAATCCTT TGTAGACGAC TTAGTTGAGG AACGGGGTAT TGTAAGCAGT    4200
AGAGTAGCCT TGTTGTTACG ATCTGCTGAG ATTAAGCCTT TGTTCCCAAG ATTTGT        4256
```

(2) INFORMATION FOR SEQ ID NO:32:

(i) SEQUENCE CHARACTERISTICS:
        (A) LENGTH: 381 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:32:

```
TCAAAAAGAA CATTTCTTCT GAGTGGTGAG GGGTCCGTTA GAGCACACTC GCTCCTTGGA     60
AGAGATGTTT TTTTGATAT  TAGGAACCAA TAGAATATTT AGAATTTAAT TTAGATTAAA    120
TTATAGAAGG GTATCTGTAG CGATAAGTTT CCATTTCAAA TTTTTCTGAT GCAGTAGTAT    180
GTTCTTTTCT AAAATAAAAT GATAGTTTAT TAATGATTAA ACTAATTATT ATCCTTTGGC    240
CATCTTTTTC TACATTTTCC AGAAACAGAT CTAATTACGT TTTTGCTATC TATAATTATT    300
AAAAATAATC ATATATCTTT AAAGTTGACC TCAACGTCTT AAAATGTTTA GTTTTTTAAT    360
TAACCCTAAA CCCTAGAACA C                                              381
```

1

DIAGNOSTIC PROBES FOR PNEUMOCYSTIS CARINI

This is a continuation application of application Ser. No. 08/298,087, filed on 31 Aug. 1994, now abandoned, which application is a continuation of Ser. No. 07/922,987, filed on 30 Jul. 1992, now abandoned.

BACKGROUND OF THE INVENTION

1. Field of the Invention

This invention relates to a method for diagnosing for *Pneumocystis carinii* by detecting the presence of a nucleic acid sequence containing the 26S rRNA gene specific for *Pneumocystis carinii*. More particularly, this invention relates to a method for diagnosing for *Pneumocystis carinii* which comprises amplifying a sample of DNA from *Pneumocystis carinii* by polymerase chain reaction (PCR) using species specific primers and detecting the PCR products with species specific radioactive or non-radioactive oligonucleotide probes. This invention also relates to a method for diagnosing for various species of *Pneumocystis carinii* by detecting the presence of a nucleic acid sequence containing the particular 16S or 26S rRNA gene sequence specific for that species of *Pneumocystis carinii*.

DESCRIPTION OF THE BACKGROUND

The disclosures referred to herein to illustrate the background of the invention and to provide additional detail with respect to its practice are incorporated herein by reference. For convenience, the disclosures are referenced in the following text and respectively grouped in the appended bibliography.

*Pneumocystis carinii* (*P. carinii*) is a ubiquitous eukaryotic microorganism causing asymptomatic infections in most humans early in childhood (1) but causing life-threatening pneumonia in immunosuppressed hosts including patients with Acquired Immune Deficiency Syndrome (AIDS, 2). Although morphologically *P. carinii* has properties associated with both protozoa and yeasts, the 16S rRNA coding sequence of *P. carinii* grown in immunosuppressed rats most resembled that of the yeast *Saccharomyces cerevisiae* (*S. cerevisiae*, 3). This sequence also included a 390 base pair insertion resembling a Group I intron, located 31 nucleotides from the 3' end of the rRNA gene (3). Absence of this sequence from mature 16S rRNA (4) and demonstration of its ability to spontaneously excise from transcripts of cloned fragments of the gene (5) confirmed its identity as a self-splicing intron (6–7). The sequence of the 5S rRNA of *P. carinii* grown in nude rats showed closer similarity to 5S rRNA of Amoeba and Myxomycota than to that of Ascomycetes such as Saccharomyces (8). However, the validity of 5S rRNA sequence analysis as a taxonomic tool has been questioned (9). In *S. cerevisiae*, the 5S rRNA is encoded in the same genomic repeated element encoding 16S, 5.8S and 26S rRNAs, but on the opposite strand (reviewed in 10), although most eukaryotes studied do not have the gene for 5S rRNA linked to those for the other rRNA species. Hybridization of chromosomal DNA separated by pulsed field electrophoresis with 16S rRNA-derived probes has localized the 16S rRNA gene of Pneumocystis to one or two 500 kbp. chromosomal DNAS, with the gene for 5S rRNA apparently located elsewhere (11–12).

BRIEF DESCRIPTION OF THE FIGURES

FIG. 2 shows the total contiguous sequence determined for *P. carinii* from immunosuppressed Sprague-Dawley rats (Sasco) by the strategy shown in FIG. 1A. Except for the last 18 nucleotides (shown in lower case), capital letters indicate rRNA coding sequences (positive strand), lower case letters indicate spacers, and underlined lower case letters indicate Group I introns. The initial 22 nucleotides are from the 3'-terminal portion of the Group I intron in 16S rRNA. Nucleotides 23–53 are the second exon of 16S rRNA, 54–216 are internal transcribed spacer 1 (ITS1), 217–374 the gene for 5.8S rRNA (identified by similarity to other 5.8S rRNA sequences), 375–556 ITS2, and 557–4256 are the gene for 26S rRNA, with a Group I intron sequence in lower case underlined. This sequence has been deposited at EMBL/GenBank under accession No. M86760.

FIG. 3 shows a comparison of the sequence of the 5.8S rRNA gene of *P. carinii* shown in FIG. 2 with the homologous sequences from *Saccharomyces cerevisiae* (23) shown as Sc, *Tetrahymena pyriformis* (*T. pyriformis*) (24) shown as Tp, and *Homo sapiens* (25) shown as Hs. Since the actual 5.8S rRNA sequence was not determined, the termini of the *P. carinii* gene have been chosen based on the known sequence of the homologous gene of *S. cerevisiae*, to which it appears to be closely related. The three nucleotides 5' to the proposed rRNA 5' terminus are shown here in lower case letters.

FIG. 5 shows a comparison of the sequence of the 26S rRNA genes of *P. carinii* (Pc) from FIG. 2, with homologous sequences from *S. cerevisiae* (Sc), and *T. pyriformis* (Tp). The Group I self-splicing introns in the *P. carinii* and *T. pyriformis* genes have been omitted. The final 18 nucleotides of the *P. carinii* sequence were determined from organisms from immunosuppressed Hooded rats as shown in FIG. 2.

FIG. 6B shows an alternative folding for the P8 helix of the intron (5) in the 16S rRNA gene.

FIG. 7 shows the sequence of the region from nucleotides 485 through 964 of the 26S rRNA gene from *P. carinii* from Sprague-Dawley rats, as shown in FIG. 5 (Pcd). This sequence was determined for three PCR products made using oligonucleotides 4016 and 2892 as primers and for PCR products made using the oligonucleotide pair 3425 and 3426, and the pair 2893 and 2982, each resulting in products partially overlapping this region. This entire sequence was thus determined on four or five isolates, with four separate sequence determinations made for each PCR product. The sequence of DNA amplified using the same primers (4016 and 2892) from *P. carinii* from Hooded rats is shown as Pc2. The homologous regions of genes from *S. cerevisiae* (Sc) and *T. pyriformis* (Tp) are also shown. The numbering is according to the 26S rRNA sequence of Pcd as in FIG. 5. The sequence denoted Pc2 has been deposited at EMBL/GenBank under accession No. 86761.

FIG. 8 shows a comparison of the sequences of the region from nucleotides 2911 through 3327 of the 26S rRNA gene of *P. carinii* (Pcd) from Sprague-Dawley rats (FIG. 5) with the homologous regions from *P. carinii* from Hooded rats (Pc2) and from *S. cerevisiae* (Sc) and *T. pyriformis* (Tp). The fragment denoted Pc1 was amplified using primers 4138 and 4170. The sequence shown for Pc2 was determined based on amplifications using primer pair 4138 and 4139 and pair 4169 and 4170, and ligation-dependent PCR amplification of a fragment extending from oligonucleotide 3427 through a PstI site 381 nucleotides past the 3' end of the 26S rRNA gene. The sequences of homologous regions of the 26S rRNA genes of *S. cerevisiae* (Sc) and *T. pyriformis* (Tp) are shown.

FIG. 10 shows the sequence of the spacer region 3' to the 26S rRNA gene of *P. carinii* from Hooded rats (FIG. 10), which was determined by ligation-dependent PCR as described in the text. The sequences shown in FIGS. 8 and 10 have been deposited at EMBL/GenBank under accession No. M86759.

SUMMARY OF THE INVENTION

Figure 1:
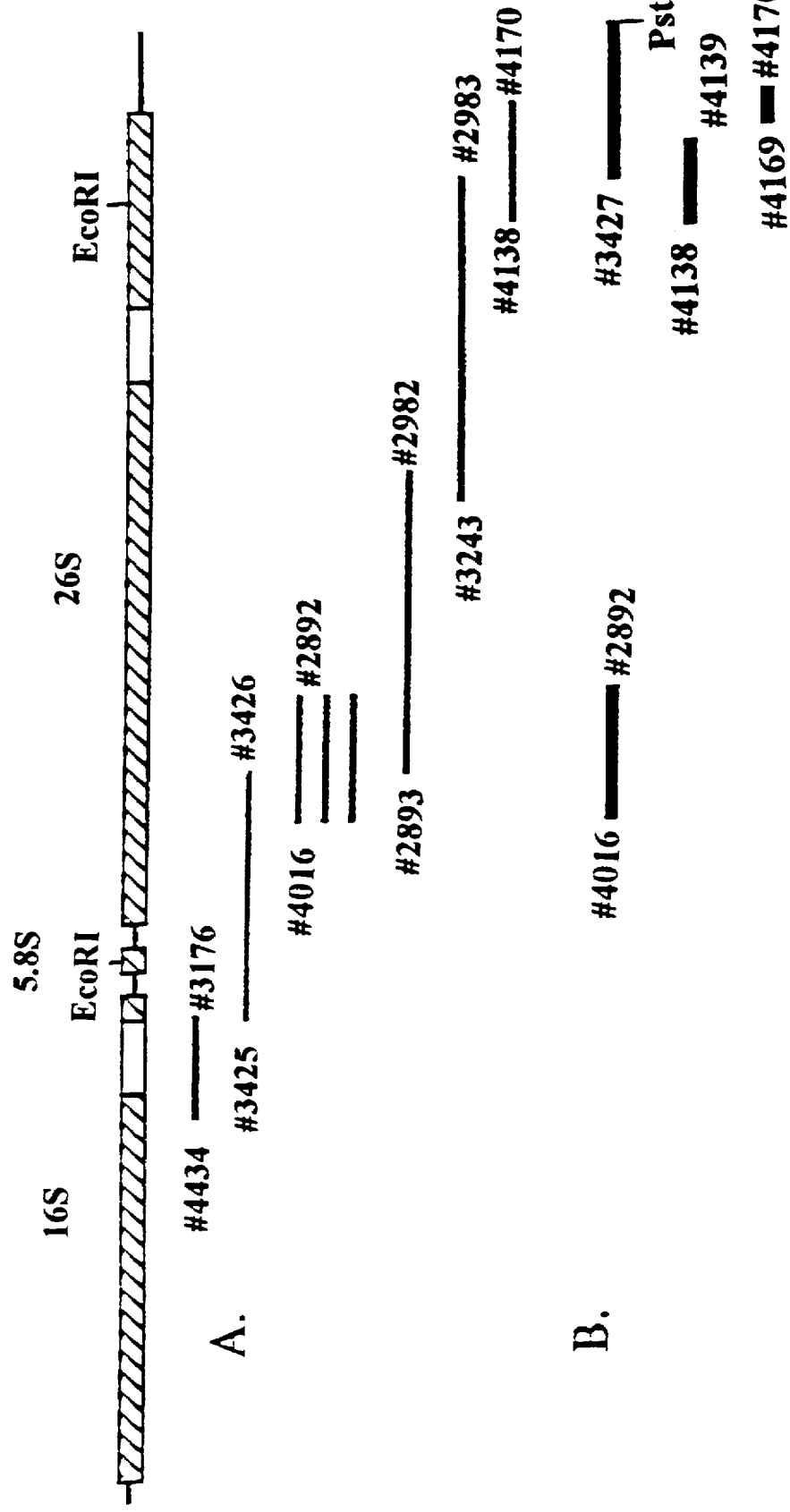
FIGS. 1A and 1B show the DNA sequence of a portion of the rRNA-encoding gene(s) of *P. carinii* isolated from immunosuppressed Sprague-Dawley rats (Sasco) and the PCR amplifications which were subsequently cloned and sequenced. The top line represents the DNA sequence of a portion of the rRNA-encoding gene(s) of *P. carinii* isolated from immunosuppressed Sprague-Dawley rats (Sasco). The horizontal lines below represent PCR amplifications which were subsequently cloned and sequenced. Thin lines (FIG. 1A) refer to PCR products from Sprague-Dawley rats (Sasco) and heavy lines (FIG. 1B) refer to PCR products from Hooded rats. Numbers refer to oligonucleotide primers (Table 1) used in each PCR reaction.
Figure 4:
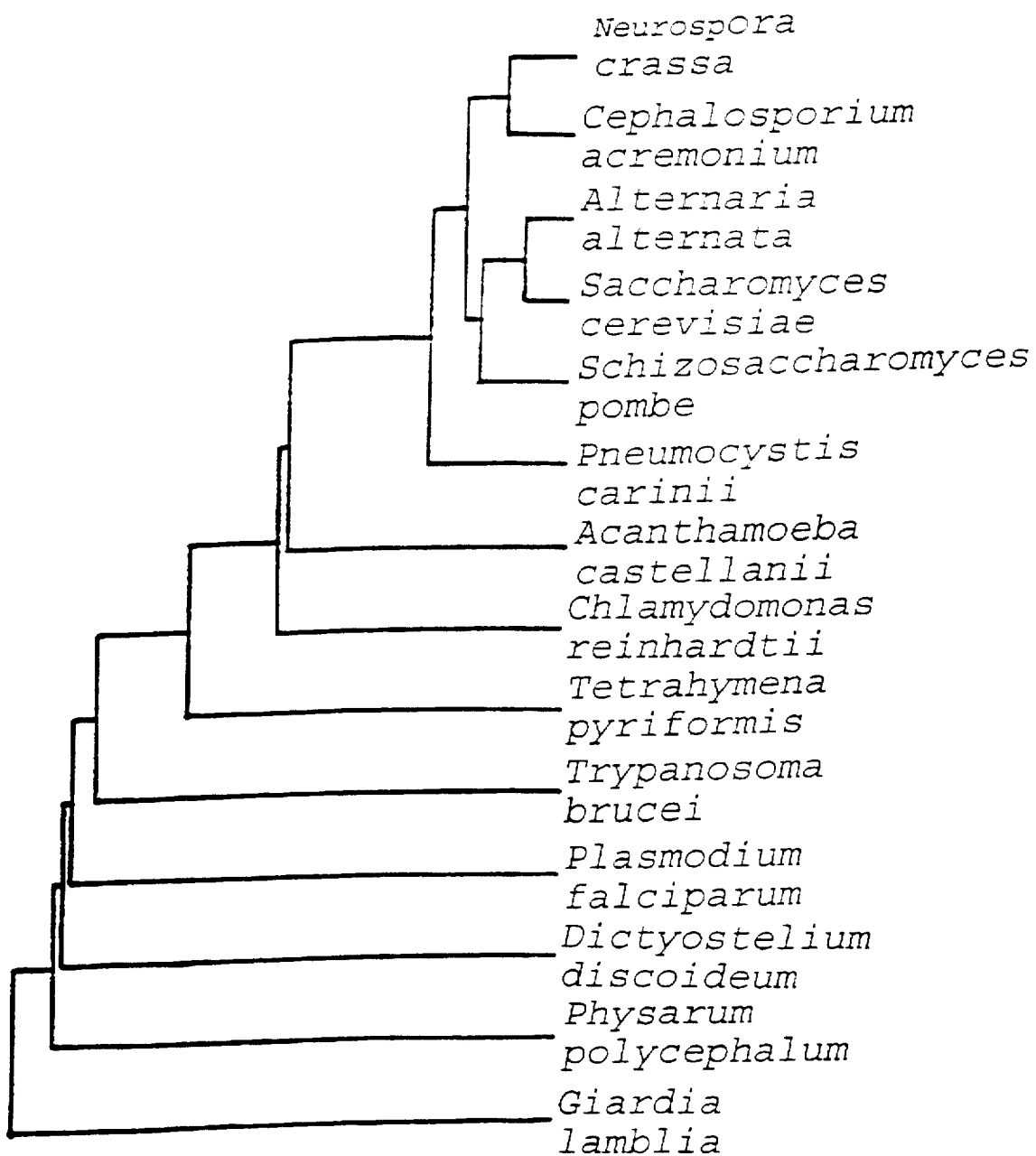
FIG. 4 is a dendrogram generated by the "pileup" program of the Wisconsin-GCG package indicating sequence similarity (but not necessarily evolutionary relationships) among the 5.8S rRNAs compared in Table II.

The present invention pertains to a method for diagnosing for *Pneumocystis carinii* which comprises detecting the presence of a nucleic acid sequence containing the 26S rRNA gene specific for *Pneumocystis carinii* in a sample which comprises the steps of:

(a) treating the sample with an oligodeoxyribonucleotide primer for each strand of the nucleic acid sequence, four different nucleoside triphosphates, and an agent for polymerization under hybridizing conditions, such that for each strand an extension product of each primer is synthesized which is sufficiently complementary to each strand of the nucleic acid sequence being detected to hybridize therewith and contains the 26S rRNA gene specific for *Pneumocystis carinii*, wherein the primers are selected such that the extension product synthesized from one primer, when it is separated from its complement, can serve as a template for synthesis of the extension product of the other primer;

(b) treating the sample from step (o) under denaturing conditions to separate the primer extension products from the templates on which they are synthesized if the sequence to be detected is present;

(c) treating the product from step (b) with oligodeoxyribonucleotide primers, four different nucleoside triphosphates, and an agent for polymerization such that a primer extension product is synthesized using each of the single strands produced in step (b) as a template, resulting in amplification of the sequence to be detected if present;

(d) hybridizing the primer extension products from step (c) with a labeled oligodeoxyribonucleotide probe complementary to the 26S rRNA gene specific for *Pneumocystis carinii*;

(e) determining whether hybridization in step (d) has occurred.

In another embodiment, the present invention pertains to a method for diagnosing for a species of *Pneumocystis carinii* which comprises detecting the presence of a nucleic acid sequence containing the 26S rRNA gene specific for that species of *Pneumocystis carinii* in a sample which comprises the steps of:

(a) treating the sample with an oligodeoxyribonucleotide primer for each strand of the nucleic acid sequence, four different nucleoside triphosphates, and an agent for polymerization under hybridizing conditions, such that for each strand an extension product of each primer is synthesized which is sufficiently complementary to each strand of the nucleic acid sequence being detected to hybridize therewith and contains the 26S rRNA gene specific for that species of *Pneumocystis carinii*, wherein the primers are selected such that the extension product synthesized from one primer, when it is separated from its complement, can serve as a template for synthesis of the extension product of the other primer;

(b) treating the sample from step (a) under denaturing conditions to separate the primer extension products from the templates on which they are synthesized if the sequence to be detected is present;

(c) treating the product from step (b) with oligodeoxyribonucleotide primers, four different nucleoside triphosphates, and an agent for polymerization such that a primer extension product is synthesized using each of the single strands produced in step (b) as a template, resulting in amplification of the sequence to be detected if present;

(d) hybridizing the primer extension products from step (c) with a labeled oligodeoxyribonucleotide probe complementary to the 26S rRNA gene specific for that species of *Pneumocystis carinii*;

(e) determining whether hybridization in step (d) has occurred.

In yet another embodiment, the present invention pertains to a method for diagnosing for a species of *Pneumocystis carinii* which comprises detecting the presence of a nucleic acid sequence containing the 16S rRNA gene specific for that species of *Pneumocystis carinii* in a sample which comprises the steps of:

(a) treating the sample with an oligodeoxyribonucleotide primer for each strand of the nucleic acid sequence, four different nucleoside triphosphates, and an agent for polymerization under hybridizing conditions, such that for each strand an extension product of each primer is synthesized which is sufficiently complementary to each strand of the nucleic acid sequence being detected to hybridize therewith and contains the 16S rRNA gene specific for that species of *Pneumocystis carinii*, wherein the primers are selected such that the extension product synthesized from one primer, when it is separated from its complement, can serve as a template for synthesis of the extension product of the other primer;

(b) treating the sample from step (a) under denaturing conditions to separate the primer extension products from the templates on which they are synthesized if the sequence to be detected is present;

(c) treating the product from step (b) with oligodeoxyribonucleotide primers, four different nucleoside triphosphates, and an agent for polymerization such that a primer extension product is synthesized using each of the single strands produced in step (b) as a template, resulting in amplification of the sequence to be detected if present;

(d) hybridizing the primer extension products from step (c) with a labeled oligodeoxyribonucleotide probe complementary to the 16S rRNA gene specific for that species of *Pneumocystis carinii*;

(e) determining whether hybridization in step (d) has occurred.

DETAILED DESCRIPTION OF THE INVENTION

This invention relates to a method for diagnosing for *Pneumocystis carinii* by detecting the presence of a nucleic acid sequence containing the 26S rRNA gene specific for *Pneumocystis carinii*. More particularly, this invention relates to a method for diagnosing for *Pneumocystis carinii* which comprises amplifying a sample of DNA from *Pneumocystis carinii* by polymerase chain reaction (PCR) using species specific primers and detecting the PCR products with species specific radioactive or non-radioactive oligonucleotide probes. This invention also relates to a method for diagnosing for various species of *Pneumocystis carinii* by detecting the presence of a nucleic acid sequence containing the particular 16S or 26S rRNA gene sequence specific for that species of *Pneumocystis carinii*.

The term "oligonucleotide" as used herein refers to primers, probes, oligomer fragments to be detected, oligomer controls, and unlabeled blocking oligomers. Oligonucleotide are molecules comprised of two or more deoxyribonucleotides or ribonucleotides.

The term "primer" as used herein refers to an oligonucleotide, preferably an oligodeoxyribonucleotide, either naturally occurring such as a purified restriction digest or synthetically produced, which is capable of acting as a point of initiation of synthesis when subjected to conditions in which synthesis of a primer extension product, which is complementary to a nucleic acid strand, is induced, i.e., in the presence of nucleotides, an agent for polymerization such as a DNA polymerase, and a suitable temperature and pH. The primer must be sufficiently long to prime the synthesis of extension products in the presence of the polymerization agent.

In accord with the method of the present invention, the sequence of the portion of the major rRNA-encoding operon (encoding the 16S, 5.8S and 26S rRNA molecules specific for *P. carinii*) from organisms derived from the lungs of immunosuppressed rats, including the genes for 5.8S and 26S rRNAs, has been determined. These two genes show similarity to the homologous genes of *S. cerevisiae*, with the gene for 26S rRNA also containing an apparent Group I self-splicing intron.

The relatedness of different Pneumocystis isolates has been difficult to determine in the absence of a long-term culture method for this organism. The 5S rRNA gene amplified by polymerase chain reaction (PCR) from multiple infected humans and rats had the identical sequences (13). However, rat and human-derived organisms showed sequence differences in their mitochondrial DNA (14). When portions of the 26S rRNA gene from two different sources were sequenced, phylogenetically variable regions of the gene were found to be different between these two organisms. This marked sequence difference between 26S rRNA gene sequences may represent differences between clones of the same species or may indicate the existence of more than one species within the genus Pneumocystis. In either case, such differences may provide a mechanism of recognizing the relationships between different individual Pneumocystis isolates for epidemiological studies. This appears to be the first such difference reported between Pneumocystis isolates in the sequence of a chromosomal gene.

The rRNA Operon of *P. carinii*

Although the exact phylogenetic relationship of *P. carinii* to other species remains unknown, the 5.8S and 26S rRNA genes, like that for 16S rRNA (3), are similar in primary sequence to the homologous genes of *S. cerevisiae*. This finding contrasts with the report that the 5S rRNA gene most resembles the sequence of the homologous genes of Amoeba or Myxomycota rather than those of the Ascomycetes (8). The organization of the major rRNA operon of *P. carinii* differs from that of *S. cerevisiae* in that for the former there is no evidence that the 5S rRNA and 16S-5.8S-26S rRNA operon genes are part of the same repeated DNA unit, based on pulsed field electrophoresis studies (11-12). Linkage of the 5S rRNA gene to genes encoding 16S rRNA or 26S rRNA by PCR techniques has not been observed. The amount of DNA obtained from *P. carinii* was limited, and so classical Southern analysis was not attempted.

The presence of Group I self-splicing introns in the 16S and 26S rRNA genes of *P. carinii* distinguishes this organism from *S. cerevisiae* and from its mammalian hosts. Since various compounds can specifically inhibit the splicing of Group I introns in vitro (31), Group I intron splicing may provide a specific target for development of new therapeutic agents against *P. carinii*.

Taxonomy of *P. carinii*

The exact taxonomic relationships of *P. carinii* remain uncertain, in part due to the limited number of eukaryotic microorganisms whose rRNA sequences are known. Furthermore, the definitions of the groups denoted as Fungi and Protozoa are so broad and imprecise that each includes very distantly related organisms. It is possible that once more organisms of this type are studied, these two groupings may prove to be inadequate, and the taxonomy of the eukaryotic microorganisms may require some redefinition. This has already proven to be the case for the aicrosporidia, which have been placed in a group distinct from all other eukaryotic microorganisms on the basis of their rRNA sequences (32).

In the absence of a long-term culture method or other tools for comparison of different *P. carinii* organisms, the number of species within the genus Pneumocystis is undefined. Antigenic differences between *P. carinii* obtained from different mammalian host species have been demonstrated (33–36), although their genetic basis is not proven. Although the 5S rRNA gene sequences of multiple human and rat isolates of *P. carinii* are identical (13), such isolates differ in the sequence of their mitochondrial DNA (14). DNA hybridization methods with a cloned DNA fragment have also suggested the non-identity of human and rat-derived *P. carinii*, with differences noted among different human, but not rat, isolates (37). Based on these results, it has been suggested that subspecies of *P. carinii* may be designated based on the hosts from which they are isolated (38).

The data presented herein show that multiple differences exist between the 26S rRNA gene sequences of *P. carinii* from Sprague-Dawley rats from Sasco which were immunosuppressed in isolation (and therefore presumably infected at some other location prior to their arrival here) and Hooded rats which were immunosuppressed here without isolation (and therefore presumably infected in this building or at some geographic location distinct from the site at which the Sprague-Dawley rats were infected). Since multiple independent PCR amplifications of portions of the 26S rRNA gene prepared from templates derived from different individual rats of the same type yielded identical sequences, there is no evidence that the differences observed between the two sources represent PCR artefacts, sequencing errors, or heterogeneity of rRNA sequences within an individual cell, as has been reported in Plasmodium species (39). This variation between different P. carinii isolates resembles that seen between different individual humans, which also occurs in regions of the 26S rRNA gene which are phylogenetically non-conserved (40). Sequence differences in rRNA genes have been suggested as defining species differences within the genus Giardia (41).

Figure 9:
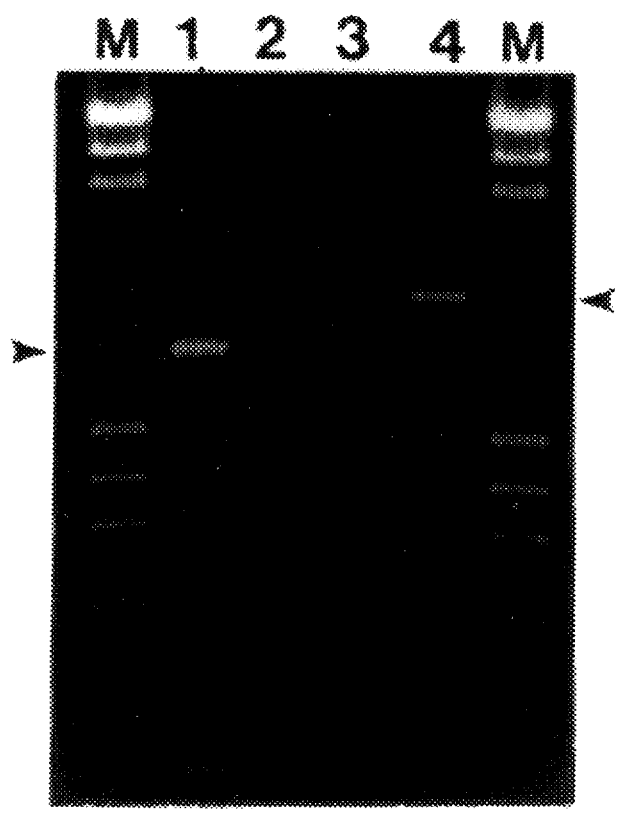
FIG. 9 shows the results of PCR amplification confirming the sequence differences between Pc1 and Pc2 shown in FIGS. 8 and 10. Primers 4358 and 4746 were used to amplify Pcd (lane 1) or Pc2 (lane2) DNA templates. Primers 4743 and 4744 were used to amplify Pc1 (lane 3) or Pc2 (lane 4) DNA. Lanes N contain a mixture of HindIII digested bacteriophage lambda DNA and HaeIII digested replicative form DNA of bacteriophage phiX174 (BRL).

When Pc1 DNA template was amplified by PCR using the primer pair 4358 (universal) and 4746 (Pc1-specific), the expected 2,067 bp product was produced; in contrast, no product was generated from Pc2 template with these same primers (FIG. 9). Similarly, primers 4743 (Pc2-specific) and 4744 (Pc2-specific) amplified an approximately 3.0 kbp product from Pc2 template; no similar product was seen with Pc1 template (FIG. 9). Note that in some reactions a barely detectable band of the same size seen with Pc2 template was seen with Pc1 template using the latter primer pair. These data are consistent with Pc1 and Pc2 each containing predominantly genes encoding single distinct major 26S rRNA sequences.

Comparisons of the sequences of multiple P. carinii rRNA gene regions should determine the extent of variability present. If different human isolates of this organism vary as much as do different rat isolates, then these sequences could be useful as epidemiological markers for identifying strains of P. carinii and studying the spread of the organism and the relative roles of new infection versus reactivation of earlier asymptomatic colonization in the development of P. carinii pneumonitis in immunosuppressed humans, including patients with AIDS. Since different species of Tetrahymena differ more in their intron sequences than in the sequences of adjacent conserved regions encoding rRNA (27), such regions may prove to be even more variable between different P. carinii organisms. Further studies may determine the variability within and between species of the internal transcribed spacers (between the 16S and 5.8S rRNA and 5.8S and 26S rRNA genes) and external transcribed spacers (flanking the rRNA coding regions). If these spacers contain regions with specific functions in rRNA transcription or processing (30), such regions may show sequence conservation.

The present invention is further illustrated by the following examples which are not intended to limit the effective scope of the claims. All parts and percentages in the examples and throughout the specification and claims are by weight of the final composition unless otherwise specified.

EXAMPLES

METHODS

Growth and Purification of *Pneumocystis carinii* Sprague-Dawley rats from Sasco, Inc. (Omaha, Neb.) were maintained in isolation cages with protective filters (Lab Products, Maplewood, N.J.) with immunosuppression by addition of dexamethasone (1 mg/ml) and tetracycline (0.5 mg/ml) to their drinking water. Water and autoclaved 8% protein diet (ICN) were provided ad libitum. Hooded rats (Harlan-Sprague-Dawley, Indianapolis, Ind.), were treated in the same way but not isolated. Rats were sacrificed after 8–12 weeks of immunosuppression or when signs of respiratory distress were observed. All subsequent procedures were done at 4° C. Each pair of lungs was removed, minced with a scissors and the homogenate was suspended in 25 ml of Dulbecco's Modified Eagle's Medium (DMEM) and centrifuged for 10 minutes at 200×g to remove tissue debris and lung cells. The supernatant was then transferred to a fresh tube, cells were collected at 1,600×g and resuspended in 3 ml of phosphate buffered saline (PBS). Suspended cells were loaded on discontinuous Percoll gradients (10–40% in 10% steps) and after centrifugation at 1,600×g for 30 minutes, trophozoites were found at the 10–20% interface, cysts with some trophozoites and a few mammalian cells at the 20–30% interface, and predominantly mammalian cells with some cysts at the 30–40% interface.

For in vitro cultivation of P. carinii, mink lung cells of line ATCC CCL64 (15) grown to 80% confluence in 10 cm petri dishes in DMEM supplemented with 10% fetal calf serum were used as feeder cells. Percoll gradient purified cysts ($5 \times 10^5$) were added to each plate in the presence of penicillin, streptomycin, gentamicin and fungizone, followed by incubation at 37° C. in a humidified 5% $CO_2$ incubator. After 1–3 days in culture, the plates were gently agitated and the Pneumocystis-containing medium was collected and centrifuged at 100×g for 5 minutes to pellet contaminating detached mammalian cells. Only a few mammalian cells detached during the culture period and these were efficiently removed by the centrifugation.

Microscopic Techniques

*Pneumocystis trophozoites* were quantitated in 5 ul samples air dried on microscope slides and stained with Diff-Quik (Baxter Healthcare Co., Miami, Fla.). Cysts were identified by toluidine blue 0 stain (16). All quantitation was done by counting three 5 ul samples for a total of 30 oil immersion fields for each sample. All cultures and purified Pneumocystis preparations were negative for fungal and bacterial contamination by microscopy and culture, and for Mycoplasma contamination by MycoTect kit (Gibco BRL).

Extraction of Nucleic Acids from Trophozoites

P. carinii cells from mink lung cell cultures were harvested by centrifugation at 3,000 rpm for 30 minutes at 4° C. in a Sorvall SS-34 rotor, and were washed with chilled PBS. Cells were resuspended in 50 mM Tris-HCl [Tris (hydroxymethyl) aminomethane hydrochloride], 50 mM Na-EDTA (sodium ethylenediaminetetraacetic acid), pH 8.0, and were lysed by incubation at 65° C. for 30 minutes in the presence of 1% SDS (sodium dodecyl sulfate). Proteins were removed by precipitation on ice in the presence of 1.25N potassium acetate followed by centrifugation at room temperature. Total nucleic acids were then concentrated by precipitation in an equal volume of absolute ethanol on ice.

Oligonucleotides

DNA oligonucleotides were synthesized by beta-cyanoethyl phosphoramidite chemistry on automated DNA synthesizers (Cyclone, Milligen and 380B, Applied Biosystems), and were purified by chromatography on NENsorb-Prep cartridges (NEN-DuPont) prior to use. Oligonucleotides used are listed in Table 1.

TABLE 1

Oligonucleotides Used for
PCR Amplifications and Sequencing

| No. | Sequence | 5' Coordinate | Ref. | |
|---|---|---|---|---|
| 228A | AACAGCTATGACCATGAT | pUC polylinker | | SEQ ID NO:1 |
| 229 | TTCCCAGTCACGACGTTG | pUC polylinker | | SEQ ID NO:2 |
| 230 | TGTAAAACGACGGCCAGT | pUC polylinker | | SEQ ID NO:3 |
| 1138 | AGGGATTGGTTGGCCTGGTCCTCCGAA | 637(+), 16S | 3 | SEQ ID NO:4 |
| 1887 | CTTTCCAGTAATAGGCTTATCG | 1726(−), 16S | 3 | SEQ ID NO:5 |
| 2892 | GCTATCCTGAGGGAAACTTCGG | 964(−), 26S | | SEQ ID NO:6 |
| 2893 | CCCGTCTTGAAACACGGACCAAGG | 635(+), 26S | | SEQ ID NO:7 |
| 2894 | CCCGCGATCAGCAAAAGCTAATCTGG | 1374(−), 16S | 3 | SEQ ID NO:8 |
| 2917 | CCATACAGAAGACCATTCTTTATCCC | 507(−), DHFR | 18 | SEQ ID NO:9 |
| 2918 | GGCCGATCAAACTCTCTTCC | 58(+), DHFR | 18 | SEQ ID NO:10 |
| 2919 | GGGAAAAGGTCGTGGGGAGCG | 977(−), TS | 17 | SEQ ID NO:11 |
| 2920 | GGGGAAGACCGCCCTGATAGG | 58(+), TS | 17 | SEQ ID NO:12 |
| 2982 | GAGCCAATCCTTATCCCGAAGTTACG | 1933(−), 26S | | SEQ ID NO:13 |
| 2983 | GTCTAAACCCAGCTCACGTTCCC | 2933(−), 26S | | SEQ ID NO:14 |
| 3175 | GGGTGGTGGTGCATGGCCG | 1262(+), 16S | 3 | SEQ ID NO:15 |
| 3176 | CCTTCCGCAGGTTCACCTACGG | 1796(−), 16S | 3 | SEQ ID NO:16 |
| 3243 | CCGCAGCAGGTCTCCAAG | 1833(+), 26S | | SEQ ID NO:17 |
| 3425 | CGAAAGAGAGGAGGTAGCACC | 368(+), intron, 16S | 5 | SEQ ID NO:18 |
| 3426 | GGTCCGTGTTTCAAGACGGG | 654(−), 26S | | SEQ ID NO:19 |
| 3427 | GGGAACGTGAGCTGGGTTTAG | 2911(+), 26S | | SEQ ID NO:20 |
| 4016 | GGTTTGGCAGGCCAACATCGG | 485(+), 26S | | SEQ ID NO:21 |
| 4138 | CCATGAAAGTGTGGCCTATCG | 2715(+), 26S | | SEQ ID NO:22 |
| 4139 | GCCTGGTCAGACAACCGC | 3049(−), 26S | | SEQ ID NO:23 |
| 4169 | GGATTATGGCTGAACGCC | 3074(+), 26S | | SEQ ID NO:24 |
| 4170 | GGCTTAATCTCAGCAGATCG | 3328(−), 26S | | SEQ ID NO:25 |
| 4358 | GACGAGGCATTTGGCTACC | 2267(−), 26S | | SEQ ID NO:26 |
| 4443 | GTACACACCGCCCGTCGC | 1631(+), 16S | 3 | SEQ ID NO:27 |
| 4743 | TTTAGCTCTTGATTGTAG | 556(+), 26S, Pc2 | | SEQ ID NO:28 |
| 4744 | CGCATATTTTATATTATG | 3234(−), 26S, Pc2 | | SEQ ID NO:29 |
| 4746 | GTTAGCTCTTGGCTTCTG | 556(+), 26S, Pc1 | | SEQ ID NO:30 |

TS refers to the thymidylate synthase (17) and DHFR refers to the dihydrofolate reductase (18) genes of *P. carinii*.

Table 1 lists all primers used for PCR amplifications and sequencing. The underlined G in 3243 was predicted for the 26S rRNA gene sequence based on sequences from other organisms, but was A in the actual 26S rRNA sequence of *P. carinii*. The underlined C in 4169 was present in the 26S rRNA gene of *P. carinii* from Hooded rats but was A in the homologous location in organisms from Sprague-Dawley rats, as described in the text. The underlined C in 3425 is from the published intron sequence (5) but was T in a clone of the intron amplified using flanking exon-derived primers 4434 and 3176.

Table II shows the extent of genetic identity as indicated by the Wisconsin-GCG "Distances" program. Sequences are from GenBank with the following accession numbers: *Neurosopora crassa*, Nc X02447; *Cephalosporium acremonium*, Ca X06574; *Alternaria alternata*, Aa X17454; *Saccharomyces cerevisiae*, Sc K01051; *Schizosaccharomyces pombe*, Sp J01359; *Pneumocystis carinii*, Pc; *Acanthamoeba castellani*, Ac K00471; *Chlamydomonas reinhardtii*, Cr M35013; *Tetrahymena pyriformis*, Tp M10752; *Trypanosoma brucei*, Tb X05682; *Plasmodium falciparum*, Pf J04683; *Dictyostelium discoideum*, Dd V00192; *Phyarum polycephalum*, Pp M13612; and *Giardia lamblia*, Gl M35013.

TABLE II

Sequence Similarity of 5.8S rRNAs of Simple Eukaryotes

| | Nc | Ca | Aa | Sc | Sp | Pc | Ac | Cr | Tp | Tb | Pf | Dd | Pp | Gl |
|---|---|---|---|---|---|---|---|---|---|---|---|---|---|---|
| Nc | 1.0000 | .9299 | .9236 | .9172 | .8599 | .8854 | .7771 | .7308 | .6883 | .6624 | .5159 | .5414 | .5097 | .4483 |
| Ca | | 1.0000 | .8924 | .8797 | .8544 | .8418 | .7215 | .7244 | .6688 | .6519 | .4873 | .5506 | .4968 | .4828 |
| Aa | | | 1.0000 | .9494 | .8987 | .8671 | .7722 | .7436 | .6883 | .6582 | .5380 | .5506 | .5161 | .4483 |
| Sc | | | | 1.0000 | .9114 | .8734 | .7848 | .7564 | .7143 | .6392 | .5316 | .5696 | .5161 | .4483 |
| Sp | | | | | 1.0000 | .8165 | .7407 | .7500 | .7143 | .5879 | .5273 | .5432 | .5290 | .4759 |
| Pc | | | | | | 1.0000 | .7468 | .7051 | .6753 | .6519 | .5063 | .5443 | .5032 | .4207 |
| Ac | | | | | | | 1.000 | .7500 | .6818 | .5679 | .5185 | .5000 | .5032 | .4828 |
| Cr | | | | | | | | 1.0000 | .6429 | .5641 | .5513 | .4744 | .4516 | .4552 |
| Tp | | | | | | | | | 1.0000 | .5844 | .5714 | .5130 | .5000 | .4414 |
| Tb | | | | | | | | | | 1.0000 | .4702 | .4691 | .5161 | .4138 |
| Pf | | | | | | | | | | | 1.0000 | .4753 | .4452 | .3793 |

TABLE II-continued

| Sequence Similarity of 5.8S rRNAs of Simple Eukaryotes | | | | | | | | | | | | | |
|---|---|---|---|---|---|---|---|---|---|---|---|---|---|
| Nc | Ca | Aa | Sc | Sp | Pc | Ac | Cr | Tp | Tb | Pf | Dd | Pp | Gl |
| | | | | | | | | | | | 1.0000 | .4065 | .3862 |
| Dd | | | | | | | | | | | | 1.0000 | .4483 |
| Pp | | | | | | | | | | | | | 1.0000 |
| Gl | | | | | | | | | | | | | |

TABLE III

| Sequence Similarity of 26S rRNAs of Simple Eukaryotes | | | | |
|---|---|---|---|---|
| | Pc | Sc | Tp | Pp |
| Pc | — | 0.833 | 0.739 | 0.623 |
| Sc | | — | 0.734 | 0.602 |
| Tp | | | — | 0.605 |

Table III shows the extent of genetic identity of 26S rRNA gene sequences, calculated as in Table II. Abbreviations are as in Table II; sequences from GenBank include Sc, J01355; Tp, X54004; and Pp, V01159.

Amplification and Cloning of DNA

*Pneumocystis carinii* DNA was amplified by means of PCR performed in a DNA Thermal Cycler (Perkin Elmer Cetus) using thermostable DNA polymerase from *Thermus aquaticus* (AmpliTaq, Perkin Elmer Cetus). Reactions were run in the presence of 0.2 mM of each dNTP, 0.4 uM of each of the indicated primers, 10 mM Tris-HCl (pH 8.3), 50 mM potassium chloride, 1.5 mM $MgCl_2$, gelatin (0.001% w/v), and 5 units of AmpliTaq DNA polymerase in 10 ul total volume. Amplifications of segments over 1 kb. were performed by incubation at 95° C. for 2 minutes followed by 30 cycles of 94° C. for 1 minute, 50° C. for 1 minute, and 72° C. for 1.5 minutes, followed by a 7 minute incubation at 72° C. Amplifications of fragments of less than 1 kb. were performed by 2 cycles of 94° C. for 2 minutes, 58° C. for 1 minute, and 72° C. for 45 seconds, followed by 30 cycles of 94° C. for 1 minute, 58° C. for 1 minute, and 72° C. for 1 minute, followed by incubation at 72° C. for 1 minute. For some PCR reactions, the thermostable DNA polymerase from *Thermus thermophilus* (Hot Tub, Amersham) was used, under reaction conditions recommended by the manufacturer using 1.5 units of polymerase in a 100 ul reaction, using 2 cycles of 94° C. for 2 minutes, 58° C. for 1 minute, and 70° C. for 2 minutes, followed by 30 cycles of 94° C. for 1 minute, 59° C. for 1 minute, and 70° C. for 3 minutes, followed by incubation at 70° C. for 10 minutes. After PCR reaction, products were purified by agarose gel electrophoresis, treated with T4 DNA polymerase (BRL) to generate blunt ends, phosphorylated with T4 polynucleotide kinase (Pharmacia), ligated under blunt end ligation conditions to SmaI-cut pUC18 DNA, and transformed into *E. coli* DH5-alpha competent cells (BRL, Bethesda, Md.) as described (19). Cells were grown in LB medium and plasmid DNA was extracted and purified as described (19).

DNA Sequence Determination

DNA sequence determination was performed on the Genesis 2,000 Automated DNA Sequencer (DuPont) according to the manufacturer's instructions for sequencing reactions run on covalently closed superhelical DNA templates, using DNA polymerase from bacteriophage T7 (Sequenase version 1.0, U.S. Biochemicals). Primers used included oligonucleotides 228A, 229, and 230 (Table 1), which base pair with regions flanking the pUC18 polylinker, and others listed in Table 1. For inserts of over 300 nucleotides without convenient internal primer binding sites, nested deletions were generated as described (19), which were then sequenced using the standard primers. All sequences reported were determined at least twice for each DNA strand.

RESULTS

Sequence of the rRNA Operon of *P. carinii*

Prior to use for these experiments, nucleic acids from *P. carinii* were shown to be from that source by confirmation of previously published sequences using PCR methods. Primers 2920 and 2919 used in a PCR reaction yielded a single 920 bP. product (based on agarose gel electrophoresis), the size predicted for the thymidylate synthase gene with its 4 intervening sequences (17). A PCR utilizing primers 2918 and 2917 amplified a single 493 bp. product, as predicted for the dihydrofolate reductase gene with a 43 bp. intervening sequence (18). The *P. carinii*-specific primers for 16S rRNA, 1138 and 2894, yielded a single PCR product of the predicted 738 bp. size (3). The "universal" 16S rRNA primers, 3175 and 3176, generated two PCR products: one was 925 bp. in length, the size predicted for the 16S rRNA gene with its Group I intron (3, 5), and the other was 535 bp. in length. This smaller fragment had a sequence identical to the corresponding region of human 18S rRNA (21), and presumably represents amplification of contaminating mink lung cell ribosomal DNA. The sequence of mink 16S rRNA is unknown, but is presumably closely related to the human sequence.

FIG. 1 shows the DNA sequence of a portion of the rRNA-encoding gene(s) of *P. carinii* isolated from immunosuppressed Sprague-Dawley rats (Sasco) and the PCR amplifications which were subsequently cloned and sequenced. The top line represents the DNA sequence of a portion of the rRNA-encoding gene(s) of *P. carinii* isolated from immunosuppressed Sprague-Dawley rats (Sasco). The horizontal lines below represent PCR amplifications which were subsequently cloned and sequenced. Thin lines (FIG. 1A) refer to PCR products from Sprague-Dawley rats (Sasco) and heavy lines (FIG. 1B) refer to PCR products from Hooded rats. Numbers refer to oligonucleotide primers (Table 1) used in each PCR reaction. Each PCR product, produced using primers listed in Table 1, was cloned into pUC18 and both strands were sequenced at least twice. All overlapping segments yielded the same sequence, indicating an error rate of Taq polymerase-catalyzed PCR (22) of less than one per 500 nucleotides. Rare misincorporation events in the regions which were only amplified once cannot be ruled out.

FIG. 2 shows the total contiguous sequence determined for *P. carinii* from immunosuppressed Sprague-Dawley rats (Sasco) by the strategy shown in FIG. 1A. Except for the last 18 nucleotides (shown in lower case), capital letters indicate rRNA coding sequences (positive strand), lower case letters indicate spacers, and underlined lower case letters indicate Group I introns. The initial 22 nucleotides are from the 3'-terminal portion of the Group I intron in 16S rRNA. Nucleotides 23–53 are the second exon of 16S rRNA, 54–216 are internal transcribed spacer 1 (ITS1), 217–374 the gene for 5.8S rRNA (identified by similarity to other 5.8S rRNA sequences), 375–556 ITS2, and 557–4256 are the gene for 26S rRNA, with a Group I intron sequence in lower case underlined. This sequence has been deposited at EMBL/GenBank under accession No. M86760. The sequence of the final exon of the 16S rRNA gene agrees with that previously reported (3), although the third base from the 3' end of the intron (C) previously reported (5) is absent in our sequence. This sequence has been confirmed in an additional amplified fragment including the entire intron sequence.

FIG. 3 shows a comparison of the sequence of the 5.8S rRNA gene of *P. carinii* shown in FIG. 2 with the homologous sequences from Saccharomyces cerevisiae (23) shown as Sc, *Tetrahymena pyriformis* (24) shown as Tp, and *Homo sapiens* (25) shown as Hs. Since the actual 5.8S rRNA sequence was not determined, the termini of the *P. carinii* gene have been chosen based on the known sequence of the homologous gene of *S. cerevisiae*, to which it appears to be closely related. The three nucleotides 5' to the proposed rRNA 5' terminus are shown here in lower case letters. The 5.8S rRNA sequence is 87% identical with the homologous rRNA of *S. cerevisiae*, which was also the species to which *P. carinii* showed closest relatedness of its 16S rRNA gene (3). In contrast, the 5.8S rRNA sequence was 67% and 69% identical with the homologous genes of *T. pyriformis* and *H. sapiens*, respectively.

FIG. 5 shows the sequence of the 26S rRNA gene from FIG. 2 compared to homologous genes from *S. cerevisiae* (26) and *T. pyriformis* (27). The indicated *P. carinii* sequence has an apparent Group I self-splicing intron sequence (see below) omitted after nucleotide 2241, and the *T. pyriformis* sequence has an intron of the same type omitted from a location four nucleotides 3' to the homologous site in the *P. carinii* gene (27). The final 18 nucleotides of the *P. carinii* sequence were determined from organisms from immunosuppressed Hooded rats as shown in FIG. 2. Thus the 26S rRNA genes of both *P. carinii* and *T. pyriformis* have Group I self-splicing introns inserted into the same relatively conserved region. Comparison of the three sequences shown in FIG. 5 indicates the relative conservation of some regions of the 26S rRNA genes, and the greater phylogenetic variability of other regions. The sequence of the coding region of the *P. carinii* 26S rRNA gene shown in FIG. 5 is 83.3% identical with the homologous gene of *S. cerevisiae* and 73.9% identical with that of *T. pyriformis*. Therefore, based upon all three genes (encoding 16S, 5.8S and 26S rRNA) of the major rRNA operon, *P. carinii* appears to be more closely related to *S. cerevisiae* than to representative "protozoa."

Group I Self-splicing Introns of rRNA Genes

As set out in FIG. 2, an apparent Group I self-splicing intron interrupts the 26S rRNA gene sequence in *P. carinii*. This intron is recognizable by the presence of the conserved P, Q, R, and S segments (boldface in FIG. 6A)) present in all introns of this class, as previously reviewed (6–7). There is 74% identity between the sequence of the putative Group I intron in the 26S rRNA gene and that previously reported (5) in the 16S rRNA gene. The entire sequence of the 16S rRNA gene intron in the *P. carinii* isolate has been confirmed, and is identical to that reported (5) except for the absence of the third nucleotide from the 3' end of the intron (C).

Figure 6A:
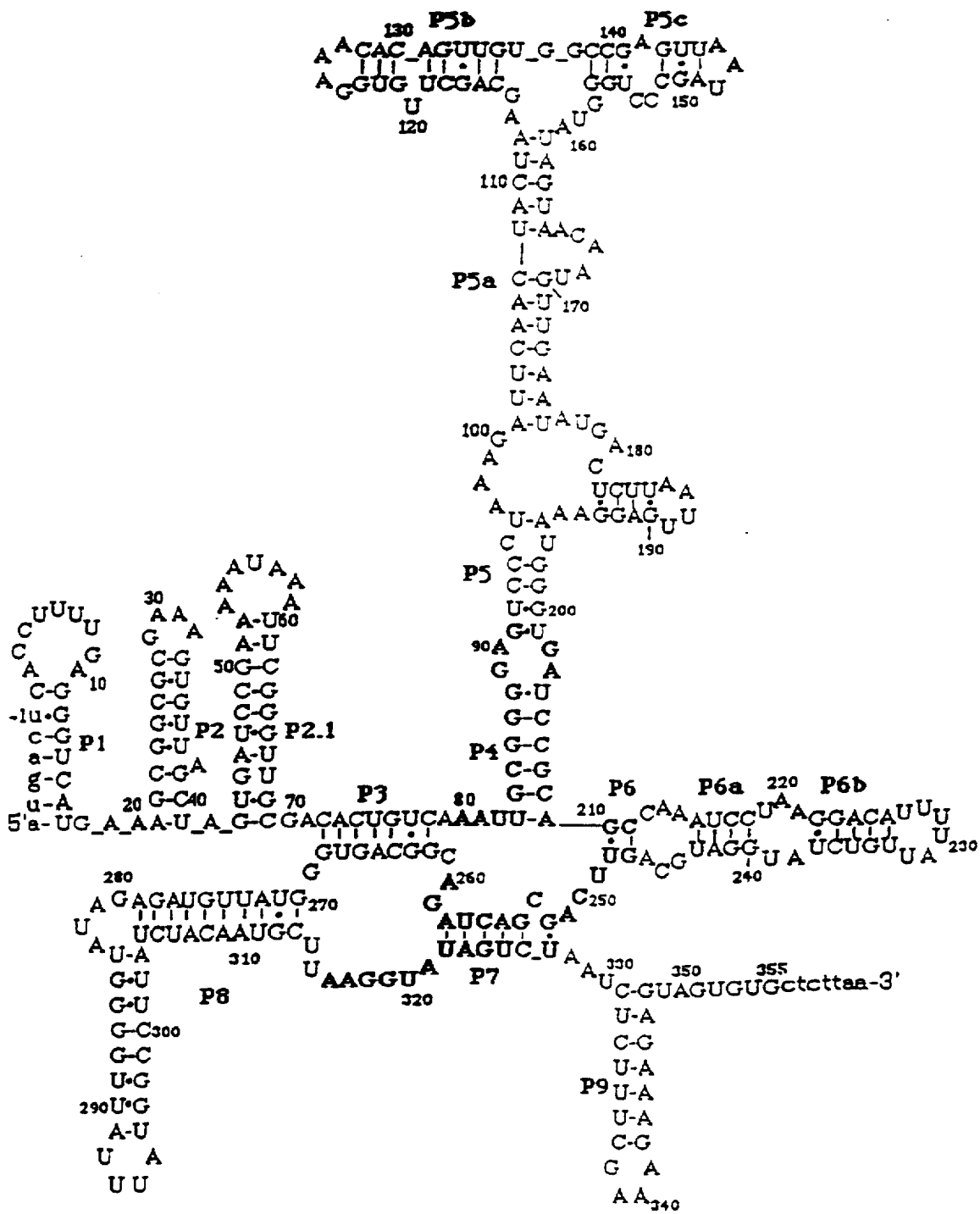
FIG. 6A shows the secondary structure into which the apparent Group I intron in the gene for 26S rRNA of *P. carinii* can be folded. The helices P1–P9 are conserved among Group I introns (6–7). The bases in the intron are numbered 1 through 355, and the flanking exon regions are shown in lower case letters. The consensus sequences P (nucleotides 80–91), Q (nucleotides 202–211), R (nucleotides 247–260) and S (nucleotides 316–327) are shown in boldface.

FIG. 6A shows the secondary structure into which the apparent Group I intron in the gene for 26S rRNA of *P. carinii* can be folded. The helices P1–P9 are conserved among Group I introns (6–7). The bases in the intron are numbered 1 through 355, and the flanking exon regions are shown in lower case letters. The consensus sequences P (nucleotides 80–91), Q (nucleotides 202–211), R (nucleotides 247–260) and S (nucleotides 316–327) are shown in boldface. FIG. 6B shows an alternative folding for the P8 helix of the intron (5) in the 16S rRNA gene.

FIG. 6A shows that the 26S rRNA gene intron can be folded into a structure similar to that reported for other Group I self-splicing introns (6–7), including that in the gene encoding 16S rRNA in *P. carinii* (5). This structure is not necessarily the most stable folded structure possible (28), but is most consistent with the consensus folding proposed for Group I introns (7). The structure in FIG. 6A contains the conserved P1 double-helix made up of a pairing of the 5' exon-intron junction with an internal guiding intron sequence (IGS). It also contains an unusually long P8 helix with a bulge-loop on its 5' side. Although the previously proposed structure for the 16S intron (5) does not have such an elongated P8 helix, its structure also can be drawn in this way (FIG. 6B).

PCR primers pairing to the exons on either side of the 26S rRNA gene intron were utilized, including a 5' primer with a 17-nucleotide 5' extension consisting of a bacteriophage SP6 promoter (29), to generate a DNA product consisting of the intron sequence with portions of both flanking exons with an SP6 promoter at the 5' end of the positive strand. Transcription of this DNA by bacteriophage SP6 RNA polymerase (Promega) results in production of RNA catalyzing self-splicing under similar conditions to those reported (5) for self-splicing of the intron in the 16S rRNA gene. Thus the three rRNA genes encoding 16S, 5.8S and 26S rRNA of *P. carinii* closely resemble their homologues in *S. cerevisiae* in sequence. However, they contain Group I self-splicing introns in the 16S and 26S rRNA genes, unlike most known fungi but like some protozoa (27).

Sequence Variation between *P. carinii* Isolates

In the course of studies to confirm the sequence shown in FIG. 2, various regions of the rRNA operon of *P. carinii* were repeatedly amplified and sequenced. Organisms obtained from the lungs of Sprague-Dawley rats (Sasco) immunosuppressed in isolation chambers yielded the same sequences for duplicate or overlapping amplifications, as summarized in FIG. 1. When portions of the 26S rDNA were amplified, cloned and sequenced from *P. carinii* obtained from Hooded rats immunosuppressed without isolation, they were found to differ in sequence from the same regions obtained from organisms from Sprague-Dawley rats from Sasco (FIGS. 7 and 8).

FIG. 7 shows the sequence of a region of the 26S rRNA gene which was determined for five independent PCR products (summarized in FIG. 1) using three different sets of primers from *P. carinii* from Sprague-Dawley rats. for the region of nucleotides 485–964 as shown in FIG. 5. This sequence is denoted Pc1 in FIG. 7, and was identical in all five determinations, including three derived using PCR primers shown by the underlined sequences in FIG. 7 and two using one primer outside this region and one within it, as shown in the legend of FIG. 7. When the pair of primers shown in FIG. 7 was used to amplify DNA from *P. carinii* from Hooded rats, the sequence shown as Pc2 was obtained. Comparison of these sequences with those of *S. cerevisiae* and *T. pyriformis* 26S rRNA sequences demonstrates that the DNA sequences of the two *P. carinii* isolates differ from each other at multiple positions, with the differences occurring mostly in phylogenetically variable regions of the rRNA sequence. However, the two *P. carinii* sequences are clearly more similar to each other than to the sequence of the *S. cerevisiae* gene, indicating the phylogenetic relatedness of these two isolates.

FIG. 8 shows a comparison of the sequences of the region from nucleotides 2911 through 3327 of the 26S rRNA gene of *P. carinii* (Pc1) from Sprague-Dawley rats (FIG. 5) with the homologous regions from *P. carinii* from Hooded rats (Pc2) and from *S. cerevisiae* (Sc) and *T. pyriformis* (Tp). The fragment denoted Pc1 was amplified using primers 4138 and 4170. The sequence shown for Pc2 was determined based on amplifications using primer pair 4138 and 4139 and pair 4169 and 4170, and ligation-dependent PCR amplification of a fragment extending from oligonucleotide 3427 through a PstI site 381 nucleotides past the 3' end of the 26S rRNA gene. The sequences of homologous regions of the 26S rRNA genes of *S. cerevisiae* (Sc) and *T. pyriformis* (Tp) are shown. The 3'-terminal region of the 26S rRNA gene of *P. carinii* from these two sources differed from each other, with most of the differences in phylogenetically non-conserved regions. Again the two *P. carinii* genes showed greater similarity to each other than to the genes from other species.

When Pc1 DNA template was amplified by PCR using the primer pair 4358 (universal) and 4746 (Pc1-specific), the expected 2,067 bp product was produced. In contrast, no product was generated from Pc2 template with these same primers (FIG. 9). Similarly, primers 4743 (Pc2-specific) and 4744 (Pc2- specific) amplified an approximately 3.0 kbp product from Pc2 template; no similar product was seen with Pc1 template (FIG. 9). Note that in some reactions a barely detectable band of the same size seen with Pc2 template was seen with Pc1 template using the latter primer pair. These data are consistent with Pc1 and Pc2 each containing predominantly genes encoding single distinct major 26S rRNA sequences.

External Transcribed Spacer Sequence

The sequence of the 26S rRNA gene shown in FIG. 3 contains a phylogenetically conserved EcoRI site at position 2875, which is located in a highly conserved region of the sequence. DNA isolated from *P. carinii* from Hooded rats was restricted with pairs of restriction enzymes, including EcoRI and various other "6-cutters," and the resulting fragments were then ligated into pUC18 cut with the same pairs of restriction enzymes. The product of each of the ligation reactions was then subjected to PCR amplification, with thermostable DNA polymerase from Thermus thermophilus (Hot Tub, Amersham) using the primer pair: oligonucleotide 3427, which pairs on the positive strand at positions 2911–2931, and oligonucleotide 230, which pairs with a pUC18 region 3' to the polylinker (on the negative strand). When such PCR reactions were analyzed by agarose gel electrophoresis with visualization of bands by ultraviolet light-induced fluorescence in the presence of ethidium bromide, only the pair of restriction enzymes EcoRI and PstI generated a visible DNA band. When this band was cloned and sequenced, its 5' region had the sequence shown as Pc2 in FIG. 8, followed by the final 18 nucleotides of the 26S rRNA gene as shown in FIG. 5 and 381 nucleotides of the following spacer region shown in FIG. 10, which would correspond to the external transcribed spacer region in the homologous operon of most eukaryotes (reviewed in 30). When the same ligation-dependent PCR procedure was followed using the DNA from *P. carinii* from Sprague-Dawley rats, no visible band of DNA was detected. This presumably indicates that the PstI site in the spacer of the DNA denoted Pc2 is absent in Pc1 DNA, and the next one is presumably too distant to support ligation-dependent PCR.

FIG. 10 shows the sequence of the spacer region 3' to the 26S rRNA gene of *P. carinii* from Hooded rats (FIG. 8), which was determined by ligation-dependent PCR. The sequences shown in FIGS. 8 and 10 have been deposited at EMBL/GenBank under accession No. 86759.

In accord with the present invention, a method is provided for diagnosing for *Pneumocystis carinii* which comprises detecting the presence of a nucleic acid sequence containing the 26S rRNA gene specific for *Pneumocystis carinii* in a sample which comprises the steps of:

(a) treating the sample with an oligodeoxyribonucleotide primer for each strand of the nucleic acid sequence, four different nucleoside triphosphates, and an agent for polymerization under hybridizing conditions, such that for each strand an extension product of each primer is synthesized which is sufficiently complementary to each strand of the nucleic acid sequence being detected to hybridize therewith and contains the 26S rRNA gene specific for *Pneumocystis carinii*, wherein the primers are selected such that the extension product synthesized from one primer, when it is separated from its complement, can serve as a template for synthesis of the extension product of the other primer;

(b) treating the sample from step (a) under denaturing conditions to separate the primer extension products from the templates on which they are synthesized if the sequence to be detected is present;

(c) treating the product from step (b) with oligodeoxyribonucleotide primers, four different nucleoside triphosphates, and an agent for polymerization such that a primer extension product is synthesized using each of the single strands produced in step (b) as a template, resulting in amplification of the sequence to be detected if present;

(d) hybridizing the primer extension products from step (c) with a labeled oligodeoxyribonucleotide probe complementary to the 26S rRNA gene specific for *Pneumocystis carinii*;

(e) determining whether hybridization in step (d) has occurred.

Amplified products may be detected by electrophoresis on agarose gels followed by hybridization with a radioactive or nonradioactive probe consisting of a third oligonucleotide specific for a sequence lying between two PCR primers on the *P. carinii* gene. The method may further comprise in steps (d) and (e) a positive control which contains the 26S rRNA gene specific for *Pneumocystis carinii* and a negative control which does not contain the 26S rRNA gene.

This invention also provides a method for diagnosing for various species of *P. carinii* by detecting the presence of a nucleic acid sequence containing the particular 16S or 26S rRNA gene sequence specific for that species of *P. carinii*. Specific PCR primers and hybridization probes for specific subtypes of *P. carinii* may be employed based on sequence analysis of different subtypes found in infected rats. Alternatively, single pairs of PCR primers based on sequences shared by all isolates may be used for strain identification if the distances between sequences shared by different isolates are distinct. This latter approach may prove useful if different strains differ in the location of the introns in their genes. Preliminary data show that this is the case for the introns in 16S rRNA in the two rat-derived P. carinii isolates described above.

Methods for amplifying and detecting nucleic acid sequences are described in detail in U.S. Pat. Nos. 4,683,195, 4,683,202, and 4,965,188, which disclosures are incorporated herein by reference.

The present invention is also directed at methods for diagnosing for Pneumocystis carinii which comprise detecting the presence of RNA complementary to a nucleic acid sequence containing the 26S rRNA gene specific for Pneumocystis carinii, the 26S rRNA gene specific for a species of Pneumocystis carinii, and the 16S rRNA gene specific for a species of Pneumocystis carinii. The methods involve using PCR to amplify mRNA sequences from cDNA. In this method, the enzyme reverse transcriptase and a primer specific for the RNA are employed to make a DNA copy of the RNA. The DNA copy may then be amplified and detected by the methods of the present invention. Examples of reverse transcriptase enzymes which may be employed include Moloney murine leukemia virus (MuLV) and Avian Myeloblastosis virus (AMV) enzymes. Methods for employing PCR to amplify mRNA sequences from cDNA are more fully described in G. Veres et al., Science, 237:415–417 (1987) and PCR Protocols; A Guide to Methods and Applications, Edited by M. A. Innis, D. H. Gelfand, J. J. Sninsky, and T. J. White, Academic Press, 1990, pp. 21–27, which disclosures are incorporated herein by reference.

Appendium of References

1. Pifer, L. L., Hughes, W. T., Stagno, S., and Woods, D. (1978) Pediatrics, 61, 35–41.
2. Hughes, W. T. (1991) Annu. Rev. Med., 42, 287–295.
3. Edman, J. C., Kovacs, J. A., Masur, H., Santi, D. V., Elwood, H. J., and Sogin, M. L. (1988) Nature, 334, 519–522.
4. Stringer, S. L., Stringer, J. R., Blase, M. A., Walzer, P. D., and Cushion, M. T. (1989) Exptal. Parasitol., 68, 450–461.
5. Sogin, M. L., and Edman, J. C. (1989) Nucleic Acids Res., 17, 5349–5359.
6. Cech, T. R. (1990) Annu. Rev. Biochem., 59, 543–568.
7. Cech, T. R. (1988) Gene, 73, 259–271.
8. Watanabe, J., Hori, H., Tanabe, K., and Nakamura, Y. (1989) Mol. Biochem. Parasitol., 32, 163–168.
9. Halanych, K. M. (1991) Mol. Biol. Evol., 8, 249–253.
10. Warner, J. (1989) Microbiol. Rev., 53, 256–271.
11. Yonagathan, T., Lin, H., and Buck, G. A. (1989). Molec. Microbiol., 3, 1473–1480.
12. Lundgren, B., Cotton, R., Lundgren, J. D., Edman, J. C., and Kovacs, J. A. (1990) Infect. Immun., 58, 1705–1710.
13. Kitada, K., Oka, S., Kimura, S., Shimada, K., Serikawa, T., Yamada, J., Tsunoo, H., Egawa, K., and Nakamura, Y. (1991) J. Clin. Microbiol., 29, 1985–1990.
14. Sinclair, K., Wakefield, A. E., Banerji, S., and Hopkin, J. M. (1991) Mol. Biochem. Parasitol., 45, 183–184.
15. Radding, J. A., Armstrong, M. Y. K., Ullu, E., and Richards, F. F. (1989) Infect. Immun., 57, 2149–2157.
16. Witebsky, F. G., Andrews, J. W. B., Gill, V. J., and MacLowry, J. D. (1988) J. Clin. Microbiol., 26, 774–775.
17. Edman, U., Edman, J. C., Lundgren, B., and Santi, D. V. (1989) Proc. Natl. Acad. Sci. USA, 86, 6503–6507.
18. Edman, J. C., Edman, U., Cao, M., Lundgren, B., Kovacs, J. A., and Santi, D. V. (1989) Proc. Natl. Acad. Sci. USA, 86, 8625–8629.
19. Sambrook, J., Fritsch, E. F., and Maniatis, T. (1989) Molecular Cloning: A Laboratory Manual, Second Edition. Cold Spring Harbor Laboratory Press, Cold Spring Harbor.
20. Torczynski, R. M., Fuke, M., and Bollon, A. P. (1985) DNA, 4, 282–291.
21. Jones, M. D., and Foulkes, N. S. (1989) Nucleic Acids Res., 17, 8387–8388.
22. Zhou, Y., Zhang, X., and Ebright, R. H. (1991) Nucleic Acids Res., 19, 6052.
23. Bell, G. I., Degennaro, L. J., Gelfand, D. H., Bishop, R. J., Valenzuela, P., and Rutter, W. J. (1977) J. Biol. Chem., 252, 8118–8125.
24. Fujiwara, H., and Ishikawa, H. (1982) Nucleic Acids Res., 10, 5173–5182.
25. Nazar, R. N., Sitz, T. O., and Busch, H. (1976) Biochemistry, 15, 505–508.
26. Georgiev, O. I., Nikolaev, N., and Hadjiolov, A. A. (1981) Nucleic Acids Res., 9, 6953–6958.
27. Nielsen, H., and Engberg, J. (1985) Nucleic Acids Res., 13, 7445–7455.
28. Zuker, M., and Stiegler, P. (1981) Nucleic Acids Res., 9, 133–148.
29. Nam, S. -C., and Kang, C. (1988) J. Biol. Chem., 263, 18123–18127.
30. Musters, W., Planta, R. J., van Heerikhuizen, H., and Raué (1990) in Hill, W. E., Dahlberg, A., Garrett, R. A., Moore, P. B., Schlessinger, D., and Warner, J. R. (eds.), The Ribosome, Amer. Soc. Microbiol., New York, pp. 435–442.
31. van Ahsen, U., Davies, J., and Schroeder, R. (1991) Nature, 353, 368–370.
32. Vossbrinck, C. R., Maddox, J. V., Friedman, S., Debrunner-Vossbrinck, P. A., and Woese, C. R. (1987) Nature, 326, 411–414.
33. Kim, H. K., Hughes, W. T., and Feldman, S. (1972) Proc. Soc. Exptal. Biol. Med., 142, 304–309.
34. Walzer, P. D., and Rutledge, M. E. (1980) J. Infect. Dis., 142, 449.
35. Gigliotti, F., Stokes, D. C., Cheatham, A. B., Davis, D. S., and Hughes, W. T. (1986) J. Infect. Dis., 154, 315–322.
36. Link, M. J., Cushion, M. T., and Walzer, P. D. (1989) Infect. Immun., 57, 1547–1555.
37. Tanabe, K., Fuchimoto, M., Egawa, K., and Nakamura, Y. (1988) J. Infect. Dis., 157, 593–596.
38. Hughes, W. T., and Gigliotti, F. (1988) J. Infect. Dis., 157, 432–433.
39. Gunderson, J. J., Sogin, M. L., Wollett, G., Hollingdale, M., de la Cruz, V. F., Waters, A. P., and McCutchan, T. F. (1987) Science, 238, 933–937.
40. Gonzalez, I. L., Gorski, J. L., Campen, T. J., Dorney, D. J., Erickson, J. M., Sylvester, J. E., and Schmickel, R. D. (1985) Proc. Natl. Acad. Sci. USA, 82, 7666–7670.
41. van Keulen, H., Campbell, S. L., Erlandsen, S. L., and Jarroll, E. L. (1991) Mol. Biochem. Parasitol., 46, 275–284.

Throughout this application, various publications have been referenced. The disclosures in these publications are incorporated herein by reference in order to more fully describe the state of the art.

The invention being thus described, it will be obvious that the same may be varied in many ways. Such variations are not to be regarded as a departure from the spirit and scope of the invention and all such modifications are intended to be included within the scope of the following claims.

We claim:

1. A method for diagnosing for *Pneumocystis carinii* which comprises detecting the presence of a nucleic acid sequence containing the 26S rRNA gene specific for *Pneumocystis carinii* in a sample which comprises the steps of:

(a) treating the sample with an oligodeoxyribonucleotide polymerase chain reaction primer for each strand of the nucleic acid sequence, four different nucleoside triphosphates, and an agent for polymerization under hybridizing conditions, such that for each strand an extension product of each primer is synthesized which is sufficiently complementary to each strand of the nucleic acid sequence being detected to hybridize therewith and contains the 26S rRNA gene specific for *Pneumocystis carinii*, wherein the primers are selected such that the extension product synthesized from one primer, when it is separated from its complement, can serve as a template for synthesis of the extension product of the other primer;

(b) treating the sample from step (a) under denaturing conditions to separate the primer extension products from the templates on which they are synthesized if the sequence to be detected is present;

(c) treating the product from step (b) with oligodeoxyribonucleotide primers, four different nucleoside triphosphates, and an agent for polymerization such that a primer extension product is synthesized using each of the single strands produced in step (b) as a template, resulting in amplification of the sequence to be detected if present;

(d) hybridizing the primer extension products from step (c) with a labeled oligodeoxyribonucleotide probe complementary to the 26S rRNA gene specific for *Pneumocystis carinii*;

(e) determining whether hybridization in step (d) has occurred to diagnose for *Pneumocystis carinii*, wherein hybridization is directly proportional to the amount of nucleic acid sequence containing the 26S rRNA gene specific for *Pneumocystis carinii* present in the sampler wherein the primers and probes are selected from the group of polynucleotides consisting of SEQ ID NOs: 6, 7, 13, 14, 17, 19–26, and 28–30.

2. The method according to claim 1, wherein in step (d) the probe is specific for a sequence lying between two polymerase chain reaction (PCR) primers on the *Pneumocystis carinii* gene.

3. The method according to claim 1, further comprising in steps (d) and (e) a positive control which contains the 26S rRNA gene specific for *Pneumocystis carinii* and a negative control which does not contain the 26S rRNA gene.

4. The method according to claim 1, wherein the nucleic acid sequence containing the 26S rRNA gene specific for *Pneumocystis carinii* is a CDNA copy of RNA.

5. A method for diagnosing for a species of *Pneumocystis carinii* which comprises detecting the presence of a nucleic acid sequence containing the 26S rRNA gene specific for that species of *Pneumocystis carinii* in a sample which comprises the steps of:

(a) treating the sample with an oligodeoxyribonucleotide polymerase chain reaction primer for each strand of the nucleic acid sequence, four different nucleoside triphosphates, and an agent for polymerization under hybridizing conditions, such that for each strand an extension product of each primer is synthesized which is sufficiently complementary to each strand of the nucleic acid sequence being detected to hybridize therewith and contains the 26S rRNA gene specific for that species of *Pneumocystis carinii*, wherein the primers are selected such that the extension product synthesized from one primer, when it is separated from its complement, can serve as a template for synthesis of the extension product of the other primer;

(b) treating the sample from step (a) under denaturing conditions to separate the primer extension products from the templates on which they are synthesized if the sequence to be detected is present;

(c) treating the product from step (b) with oligodeoxyribonucleotide primers, four different nucleoside triphosphates, and an agent for polymerization such that a primer extension product is synthesized using each of the single strands produced in step (b) as a template, resulting in amplification of the sequence to be detected if present;

(d) hybridizing the primer extension products from step (c) with a labeled oligodeoxyribonucleotide probe complementary to the 26S rRNA gene specific for that species of *Pneumocystis carinii*;

(e) determining whether hybridization in step (d) has occurred to diagnose for *Pneumocystis carinii*, wherein hybridization is directly proportional to the amount of nucleic acid sequence containing the 26S rRNA gene specific for that species of *Pneumocystis carinii* present in the sample;

wherein the primers and probes are selected from the group of polynucleotides consisting of SEQ ID NOs: 6, 7, 13, 14, 17, 19–26, and 28–38.

6. The method according to claim 5, wherein in step (d) the probe is specific for a sequence lying between two polymerase chain reaction (PCR) primers on the *Pneumosystis carinii* gene.

7. The method according to claim 5, further comprising in steps (d) and (e) a positive control which contains the 26S rRNA gene specific for *Pneumocystis carinii* and a negative control which does not contain the 26S rRNA gene.

8. The method according to claim 5, wherein the nucleic acid sequence containing the 26S rRNA gene specific for that species of *Pneumocystis carinii* is a cDNA copy of RNA.

9. A method for diagnosing for a species of *Pneumocystis carinii* which comprises detecting the presence of a nucleic acid sequence containing the 16S rRNA gene specific for that species of *Pneumocystis carinii* in a sample which comprises the steps of:

(a) treating the sample with an oligodeoxyribonucleotide polymerase chain reaction primer for each strand of the nucleic acid sequence, four different nucleoside triphosphates, and an agent for polymerization under hybridizing conditions, such that for each strand an extension product of each primer is synthesized which is sufficiently complementary to each strand of the nucleic acid sequence being detected to hybridize therewith and contains the 16S rRNA gene specific for that species of *Pneumocystis carinii*, wherein the primers are selected such that the extension product synthesized from one primer, when it is separated from its complement, can serve as a template for synthesis of the extension product of the other primer;

(b) treating the sample from step (a) under denaturing conditions to separate the primer extension products from the templates on which they are synthesized if the sequence to be detected is present;

(c) treating the product from step (b) with oligodeoxyribonucleotide primers, four different nucleoside triphosphates, and an agent for polymerization such that a primer extension product is synthesized using each of the single strands produced in step (b) as a template, resulting in amplification of the sequence to be detected if present;

(d) hybridizing the primer extension products from step (c) with a labeled oligodeoxyribonucleotide probe complementary to the 16S rRNA gene specific for that species of *Pneumocystis carinii*;

(e) determining whether hybridization in step (d) has occurred to diagnose for *Pneumocystis carinii*, wherein hybridization is directly proportional to the amount of nucleic acid sequence containing the 16S rRNA gene specific for that species of *Pneumocystis carinii* present in the sample;

wherein the primers and probes are selected from the group of polynucleotides consisting of SEQ ID NOs: 4, 5, 15, 16, 18, and 27.

10. The method according to claim 9, wherein in step (d) the probe is specific for a sequence lying between two polymerase chain reaction (PCR) primers on the *Pneumocystis carinii* gene.

11. The method according to claim 9, further comprising in steps (d) and (e) a positive control which contains the 16S rRNA gene specific for *Pneumocystis carinii* and a negative control which does not contain the 16S rRNA gene.

12. The method according to claim 9, wherein the nucleic acid sequence containing the 16S rRNA gene specific for that species of *Pneumocystis carinii* is a cDNA copy of RNA.

* * * * *